(12) United States Patent
Kathirgamanathan et al.

(10) Patent No.: US 7,718,275 B2
(45) Date of Patent: *May 18, 2010

(54) ELECTROLUMINESCENT MATERIALS AND DEVICES

(75) Inventors: Poopathy Kathirgamanathan, North Harrow (GB); Sivagnanasundram Surendrakumar, Middlesex (GB); Patrick Gemmell, Monmouthshire (GB); Subramaniam Ganeshamurugan, London (GB); Muttullingham Kumaraverl, Middlesex (GB); Arumugam Partheepan, Surrey (GB); Sutheralingam Suresh, London (GB); Selvadural Selvaranjan, Surrey (GB)

(73) Assignee: Merck Patent GmbH, Darmstadt (DE)

( * ) Notice: Subject to any disclaimer, the term of this patent is extended or adjusted under 35 U.S.C. 154(b) by 729 days.

This patent is subject to a terminal disclaimer.

(21) Appl. No.: 10/537,315

(22) PCT Filed: Dec. 5, 2003

(86) PCT No.: PCT/GB03/05303

§ 371 (c)(1),
(2), (4) Date: Aug. 22, 2005

(87) PCT Pub. No.: WO2004/050793

PCT Pub. Date: Jun. 17, 2004

(65) Prior Publication Data

US 2006/0035110 A1   Feb. 16, 2006

(30) Foreign Application Priority Data

Dec. 5, 2002   (GB) ................................ 0228335.6

(51) Int. Cl.
H01L 51/54 (2006.01)
(52) U.S. Cl. ................. 428/690; 428/917; 313/504; 313/506
(58) Field of Classification Search ........... 428/690, 428/917; 427/58, 66; 313/502–509; 257/40, 257/88–103, E51.001–E51.052; 252/301.16–301.35; 548/101, 105–106; 546/2
See application file for complete search history.

(56) References Cited

U.S. PATENT DOCUMENTS

| 5,456,988 | A | * | 10/1995 | Sano et al. ................. 428/690 |
| 7,211,334 | B2 | * | 5/2007 | Kathirgamanathan et al. .................. 428/690 |
| 2004/0027821 | A1 | | 2/2004 | Pillow et al. |

FOREIGN PATENT DOCUMENTS

| WO | WO 9858037 | * | 12/1998 |
| WO | WO 00/79616 | | 12/2000 |
| WO | WO 02/20692 | * | 3/2002 |

OTHER PUBLICATIONS

Akama et al. "Thermal decompositions of complexes of Al, Ga, In, Cr, Fe and Bi ions with 1-phenyl-3-methyl-4-benzoyl-5-pyrazolone," Journal of Thermal Analysis and Calorimetry, vol. 44, No. 5, pp. 1107-1112, May 1995.*
Gao et al., "Photoluminescence and electroluminescence of a series of terbium complexes," Synthetic Metals, vol. 99, No. 2, pp. 127-132, Feb. 1999.*
Marchetti, Fabio, "Zinc and cadmium derivatives containing several 4-acyl-5-pyrazolonate donors and additional ancillary ligands," Main Group Metal Chemistry, vol. 24, No. 5, pp. 257-266, 2001.*
Van Slyke et al., "Organic electroluminescent devices with improved stability," Applied Physics Letters, vol. 69, No. 5, pp. 2160-2162, Oct. 1996.*
Marchetti et al., "Copper and calcium complexes with the anionic O2-donor 4-tert-butylacetyl-3-methyl-1-phenylpyrazol-5-onato (Q-). Influence of hydrogen-bond interactions on lattice architecture in the crystal structures of [CuQ2(H2O)] and [CaQ2(EtOH)2]," Journal of the Chemical Society, Dalton Transactions, pp. 3325-3333, 1998.*
Qiu et al., "Photostability and morphological stability of hole transporting materials used in organic electroluminescence," Thin Solid Films, vol. 372, No. 1-2, pp. 265-270, Sep. 2000.*
Xin et al.: "Photoluminescence and electroluminescence of the exciplex formed between a terbium ternary complex and N,N'-diphenyl . . . "Phys Chem Chem Phys, 2002, 4(23), 5895-98.
Fadeeva et al.: "Mechanism of scandium and zirconium ion extraction by beta-diketones . . . " Chem Abstracts Service, XP002276191, (1975).

* cited by examiner

Primary Examiner—Marie R. Yamnitzky
(74) Attorney, Agent, or Firm—David Silverstein; Andover-IP-Law

(57) ABSTRACT

An electroluminescent material is a metal complex of 1-phenyl-3-methyl-4-trimethylacetyl-pyrazol-5-one of formula (I). An electroluminescent device comprising the compound of formula (I) in the luminescent layer is also part of the invention.

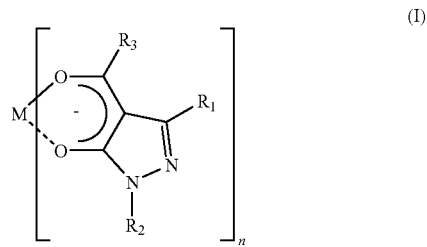

6 Claims, 23 Drawing Sheets

α-NPB

β-NPD mTADATA

Alq

Bebq

BAlq1

ZnPBO

ZnPBT

DTVbi

Device 3

Spectral radiance Peak @ 536nm

Device 4

ELECTROLUMINESCENT MATERIALS AND DEVICES

CROSS-REFERENCE TO RELATED APPLICATIONS

This application is a national stage application of international application PCT/GB03/05303 filed Dec. 5, 2003, which claims the benefit of the filing date of United Kingdom application no. 0228335.6 filed Dec. 5, 2002.

The present invention relates to electroluminescent materials and devices incorporating electroluminescent materials.

Materials which emit light when an electric current is passed through them are well known and used in a wide range of display applications. Liquid crystal devices and devices which are based on inorganic semiconductor systems are widely used; however these suffer from the disadvantages of high energy consumption, high cost of manufacture, low quantum efficiency and the inability to make flat panel displays.

Organic polymers have been proposed as useful in electroluminescent devices, but it is not possible to obtain pure colours; they are expensive to make and have a relatively low efficiency.

Another compound which has been proposed is aluminium quinolate, but this requires dopants to be used to obtain a range of colours and has a relatively low efficiency.

Patent application WO98/58037 describes a range of lanthanide complexes which can be used in electroluminescent devices which have improved properties and give better results. Patent Applications PCT/GB98/01773, PCT/GB99/03619, PCT/GB99/04030, PCT/GB99/04024, PCT/GB99/04028, PCT/GB00/00268 describe electroluminescent complexes, structures and devices using rare earth chelates.

Hitherto electroluminescent metal complexes have been based on a rare earth, transition metal, lanthanide or an actinide or have been quinolates such as aluminium quinolate.

DETAILED DESCRIPTION OF THE INVENTION

According to the invention there is provided an electroluminescent compound which has the formula

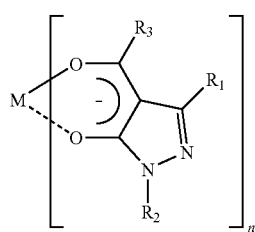

(I)

where M is a metal other than aluminium; n is the valency of M; $R_1$, $R_2$ and $R_3$ which may be the same or different are selected from hydrogen, hydrocarbyl groups, substituted and unsubstituted aliphatic groups substituted and unsubstituted aromatic, heterocyclic and polycyclic ring structures, fluorocarbons such as trifluoryl methyl groups, halogens such as fluorine or thiophenyl groups or nitrile; $R_1$, and $R_3$ can also be form ring structures and $R_1$, $R_2$ and $R_3$ can be copolymerisable with a monomer, e.g. styrene.

The compounds of formula (I) can be coordinated with a neutral ligand such as $L_p$ To form a complex

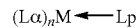

where Lα is of formula

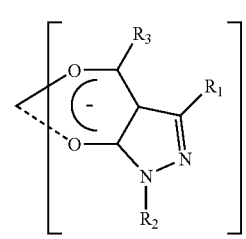

(II)

where M is a metal, n is the valency of M and Lp is a neutral ligand.

The groups $L_P$ can be selected from

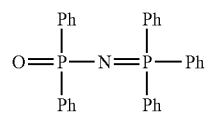

Figure 8:
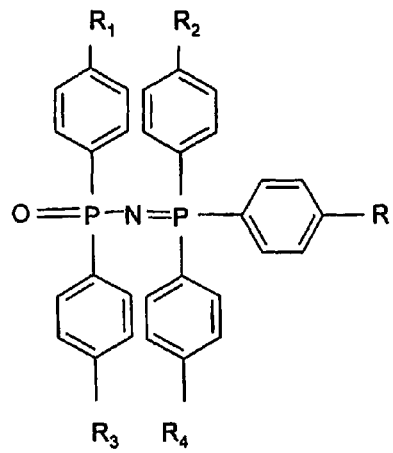
FIGS. 8-10 are formulae drawings for ligands Lp in accordance with this invention.
Figure 9B:
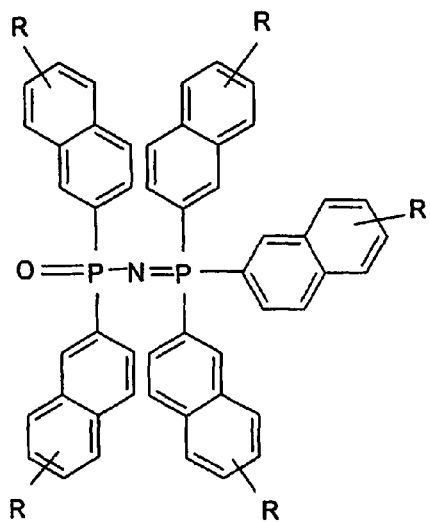
Figure 9A:
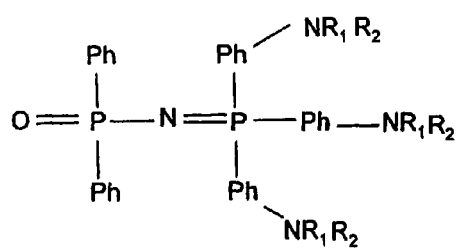

(III)

Where each Ph which can be the same or different and can be a phenyl (OPNP) or a substituted phenyl group, other substituted or unsubstituted aromatic group, a substituted or unsubstituted heterocyclic or polycyclic group, a substituted or unsubstituted fused aromatic group such as a naphthyl, anthracene, phenanthrene or pyrene group. The substituents can be for example an alkyl, aralkyl, alkoxy, aromatic, heterocyclic, polycyclic group, halogen such as fluorine, cyano, amino. Substituted amino etc. Examples are given in FIGS. 8 and 9 of the drawings where R, $R_1$, $R_2$, $R_3$ and $R_4$ can be the same or different and are selected from hydrogen, hydrocarbyl groups, substituted and unsubstituted aromatic, heterocyclic and polycyclic ring structures, fluorocarbons such as trifluoryl methyl groups, halogens such as fluorine or thiophenyl groups; R, $R_1$, $R_2$, $R_3$ and $R_4$ can also form substituted and unsubstituted fused aromatic, heterocyclic and polycyclic ring structures and can be copolymerisable with a monomer e.g. styrene. R, $R_1$, $R_2$, $R_3$ and $R_4$ can also be unsaturated alkylene groups such as vinyl groups or groups

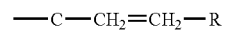

where R is as above.

$L_p$ can also be compounds of formulae

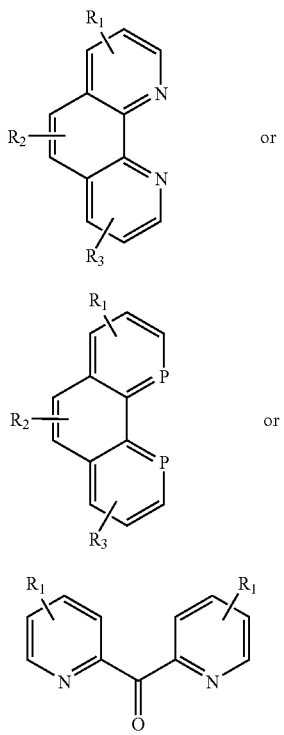

(IV)

(V)

Figure 10:
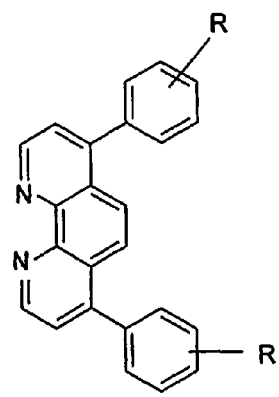
Figure 11A:
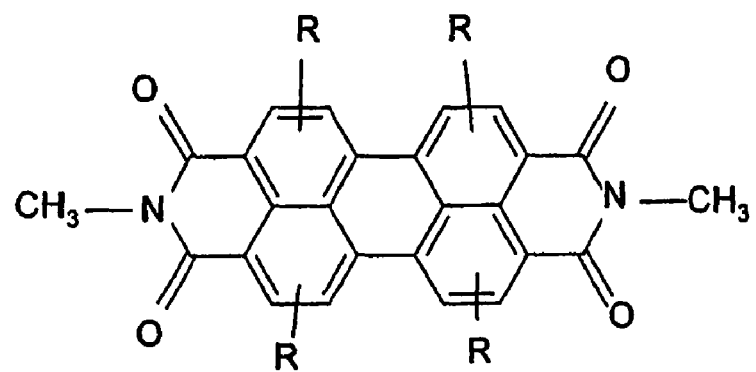
FIGS. 11-15 are formulae drawings for further ligands Lp in accordance with this invention.
Figure 11A:
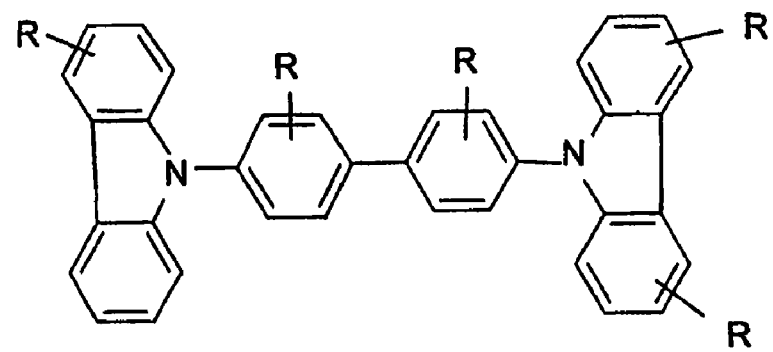
Figure 11A:
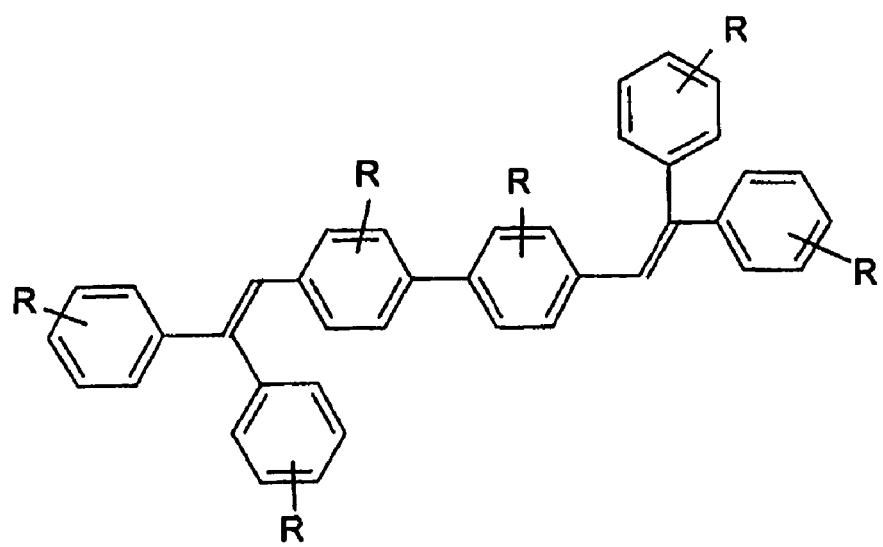
Figure 11B:
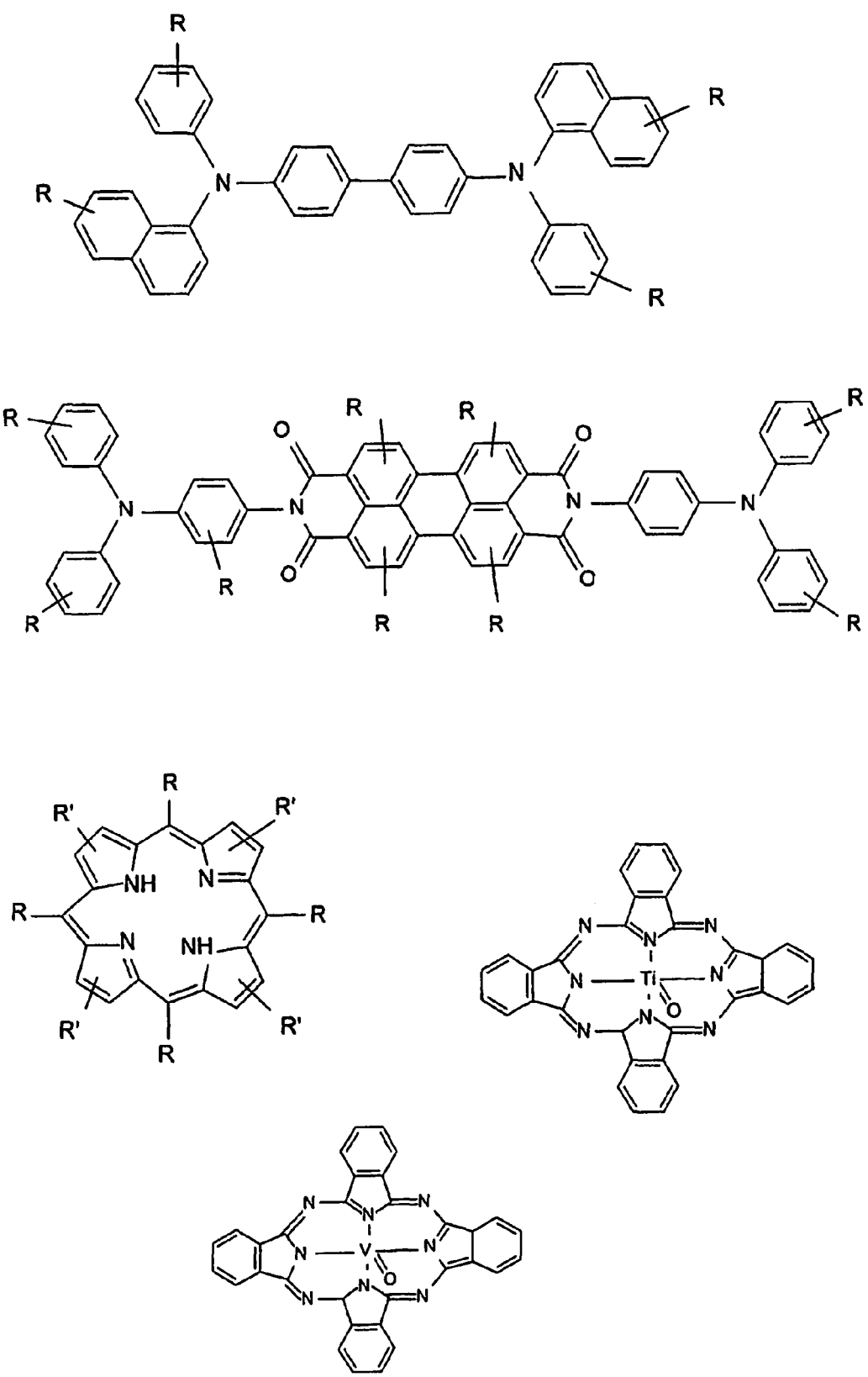
Figure 11C:
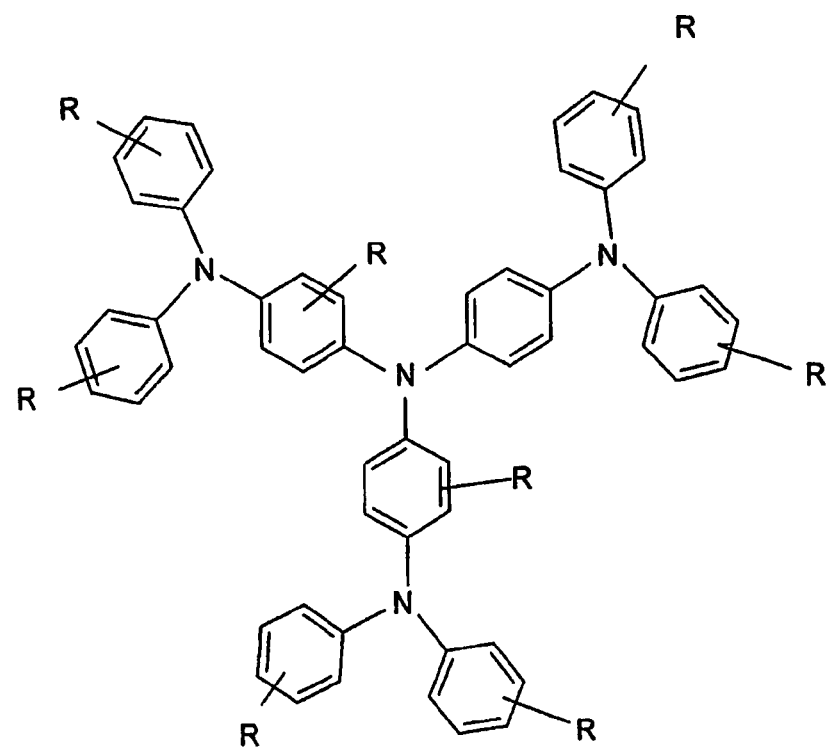
Figure 11C:
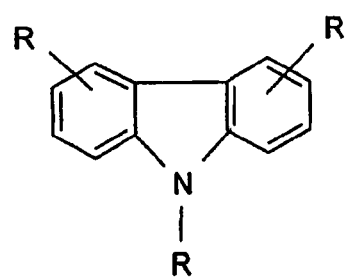
Figure 11C:
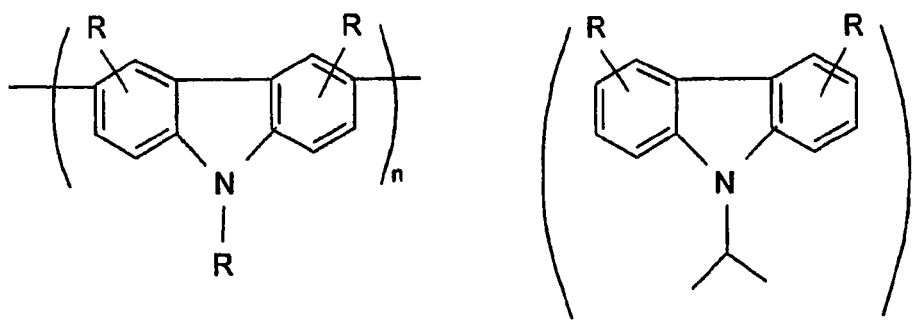

(VI)

where $R_1$, $R_2$ and $R_3$ are as referred to above, for example bathophen shown in FIG. 10 of the drawings in which R is as above or

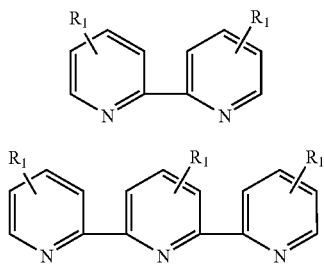

(VII)

(VIII)

where $R_1$, $R_2$ and $R_3$ are as referred to above.
$L_p$ can also be

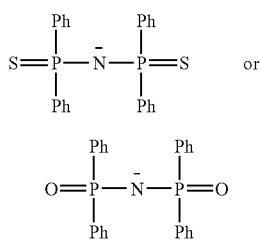

(IX)

(X)

where Ph is as above.

Figure 12A:
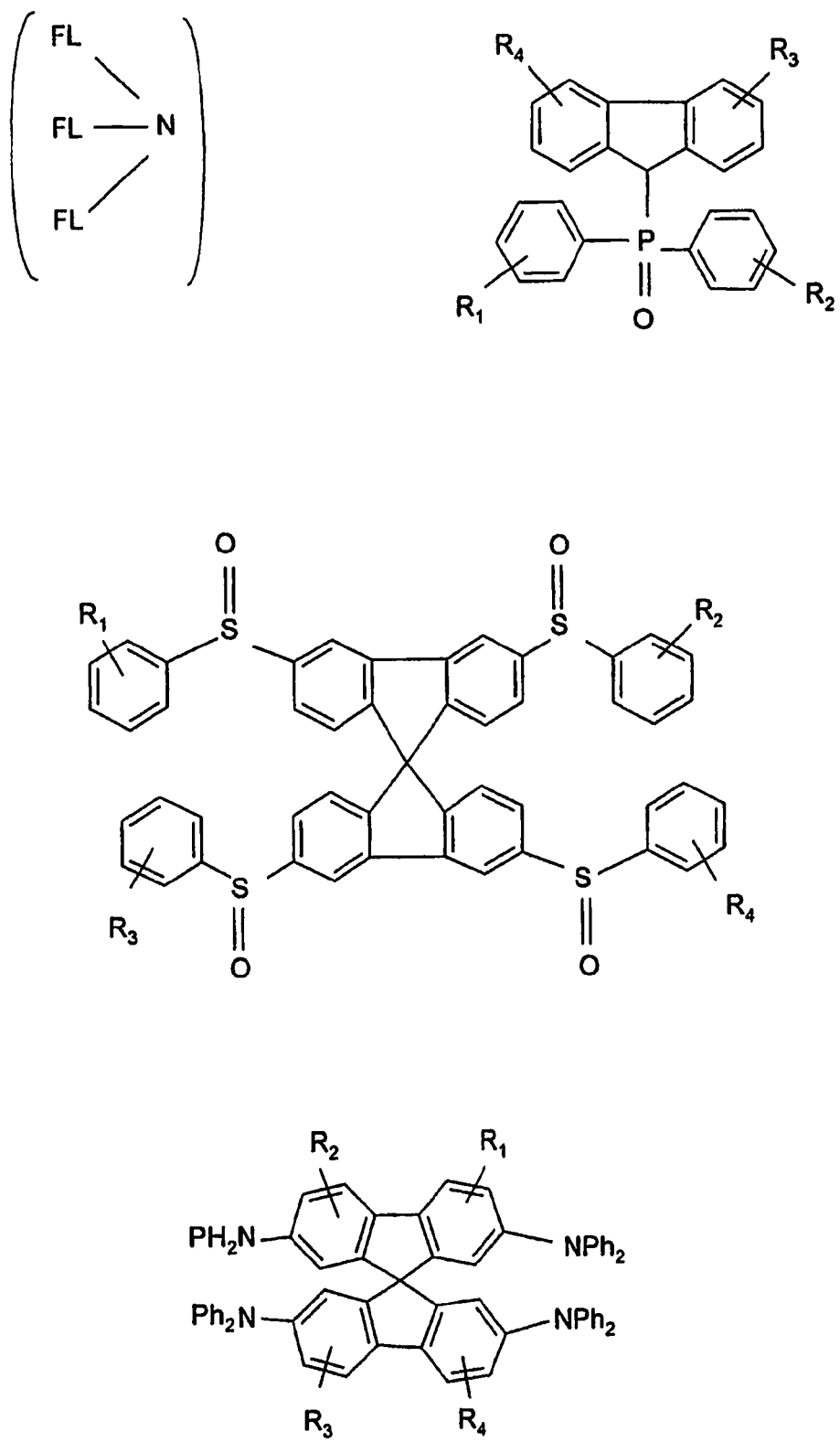
Figure 12B:
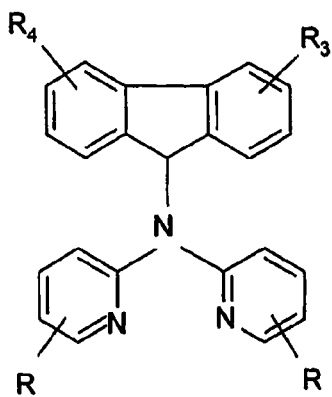
Figure 12C:
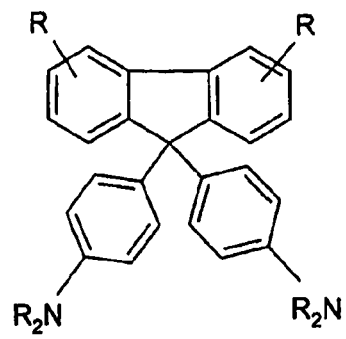
Figure 13A:
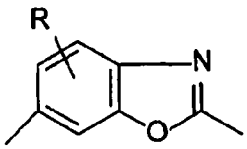
Figure 13B:
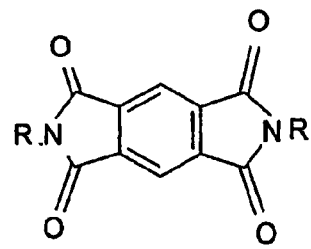
Figure 13C:
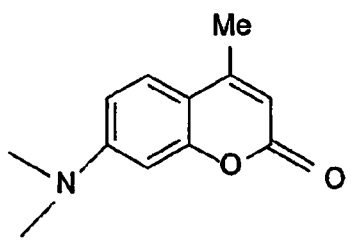
Figure 13D:
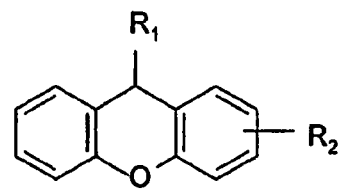
Figure 13E:
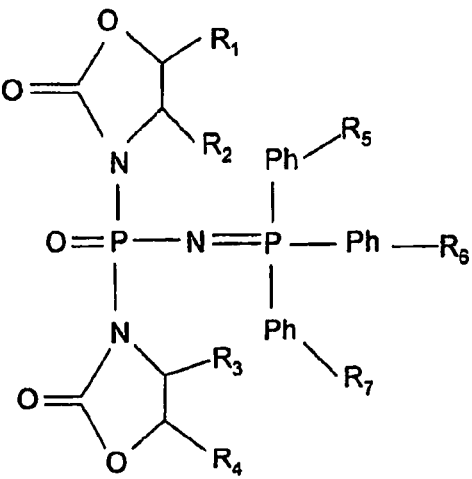
Figure 14:
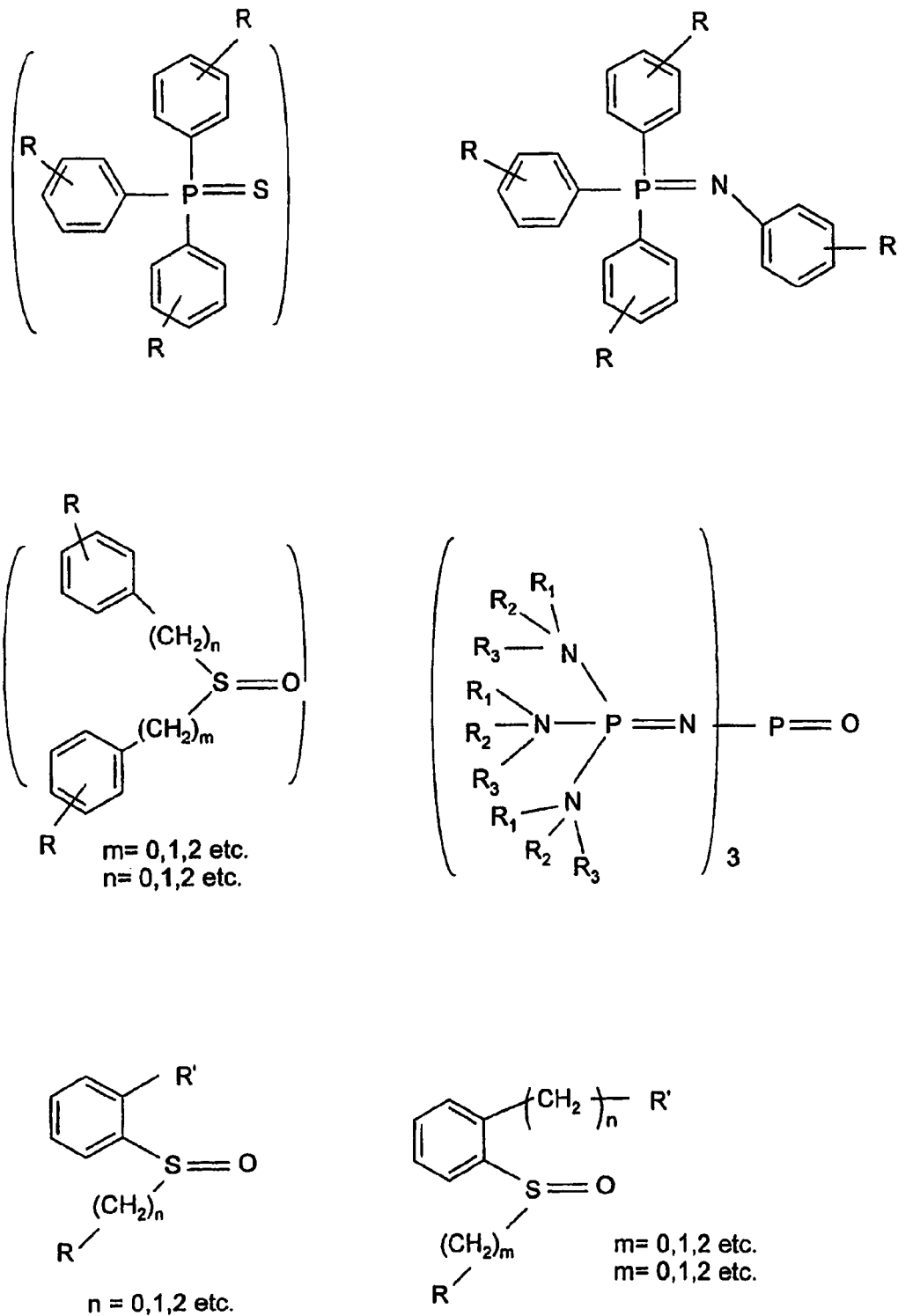
Figure 15:
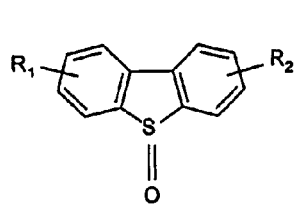
Figure 15:
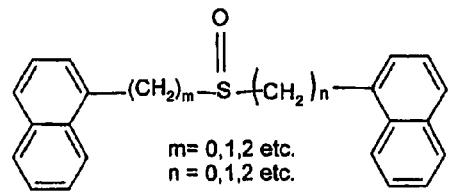
Figure 15:
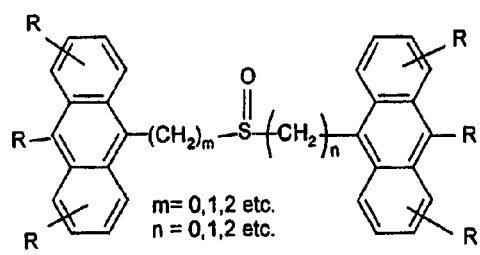
Figure 15:
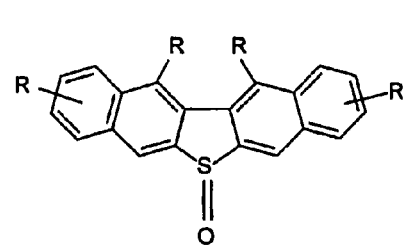
Figure 15:
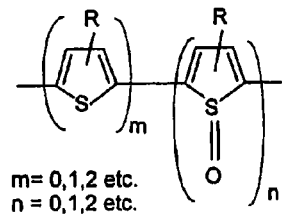
Figure 15:
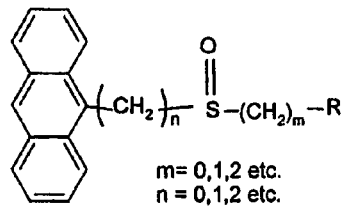
Figure 15:
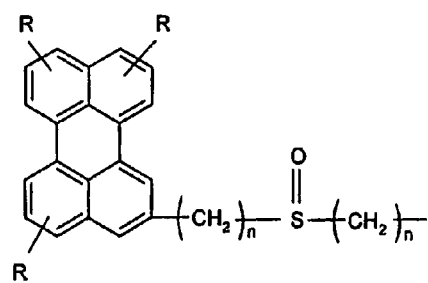
Figure 15:
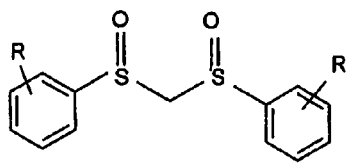
Figure 16:
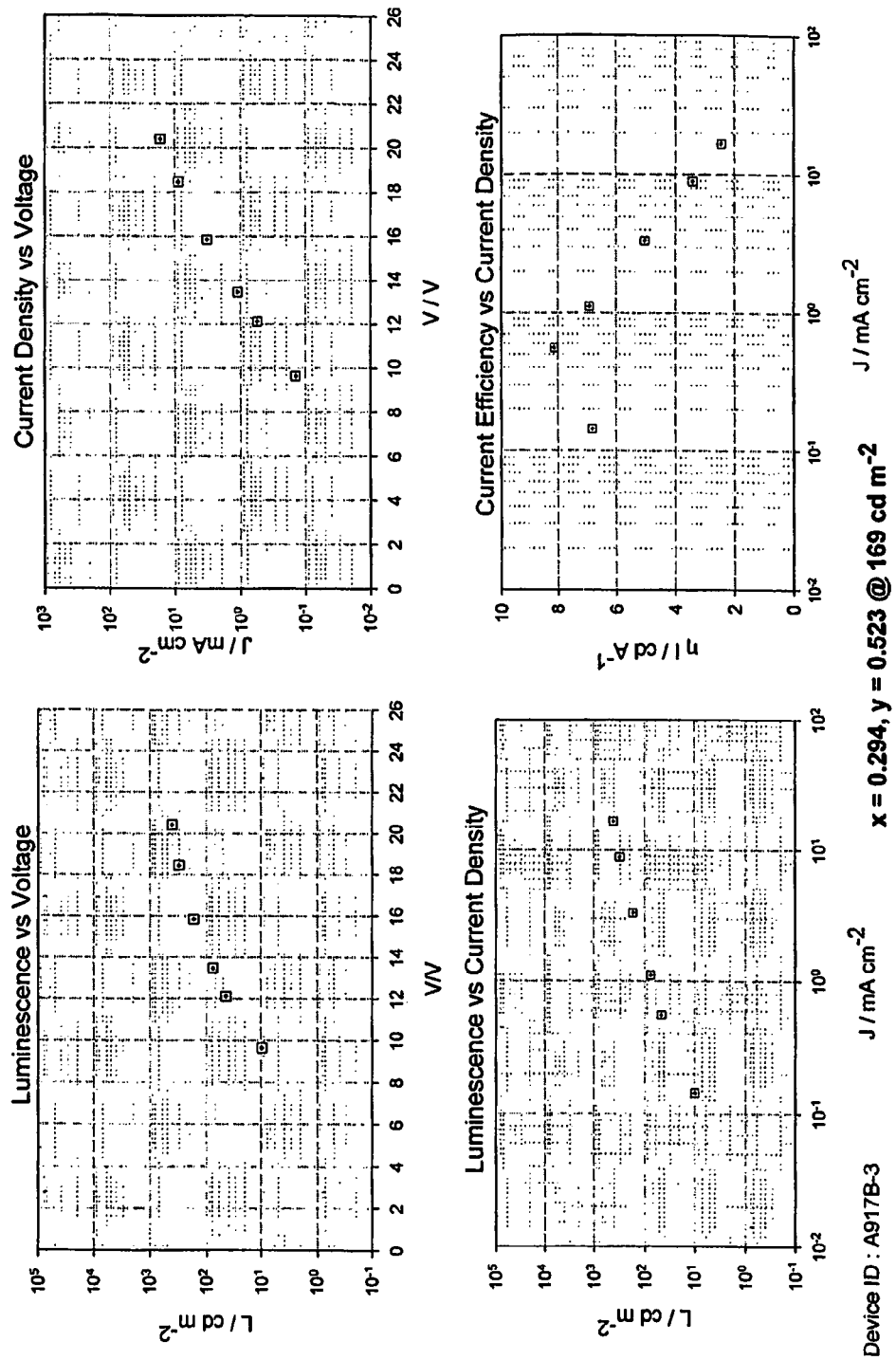
FIGS. 16-23 are graphs showing performance data and spectra obtained using electroluminescent devices according to this invention.
Figure 17:
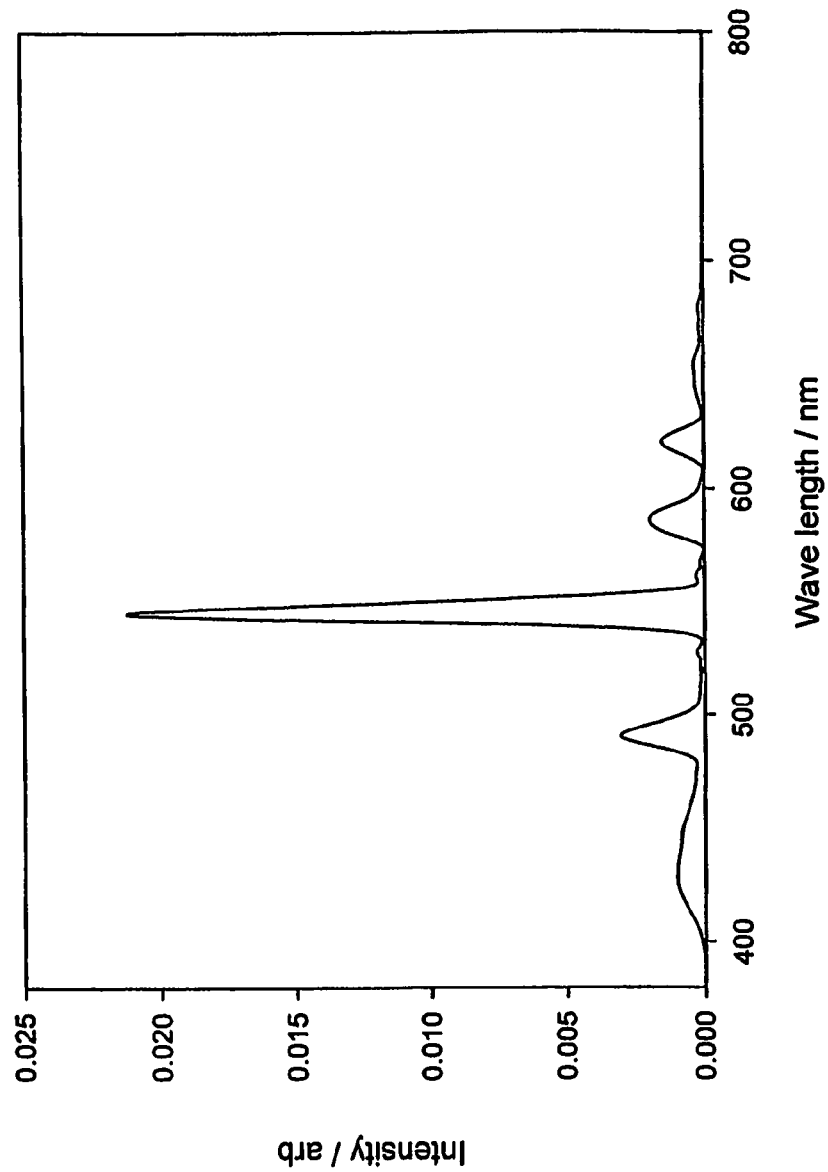
Figure 18:
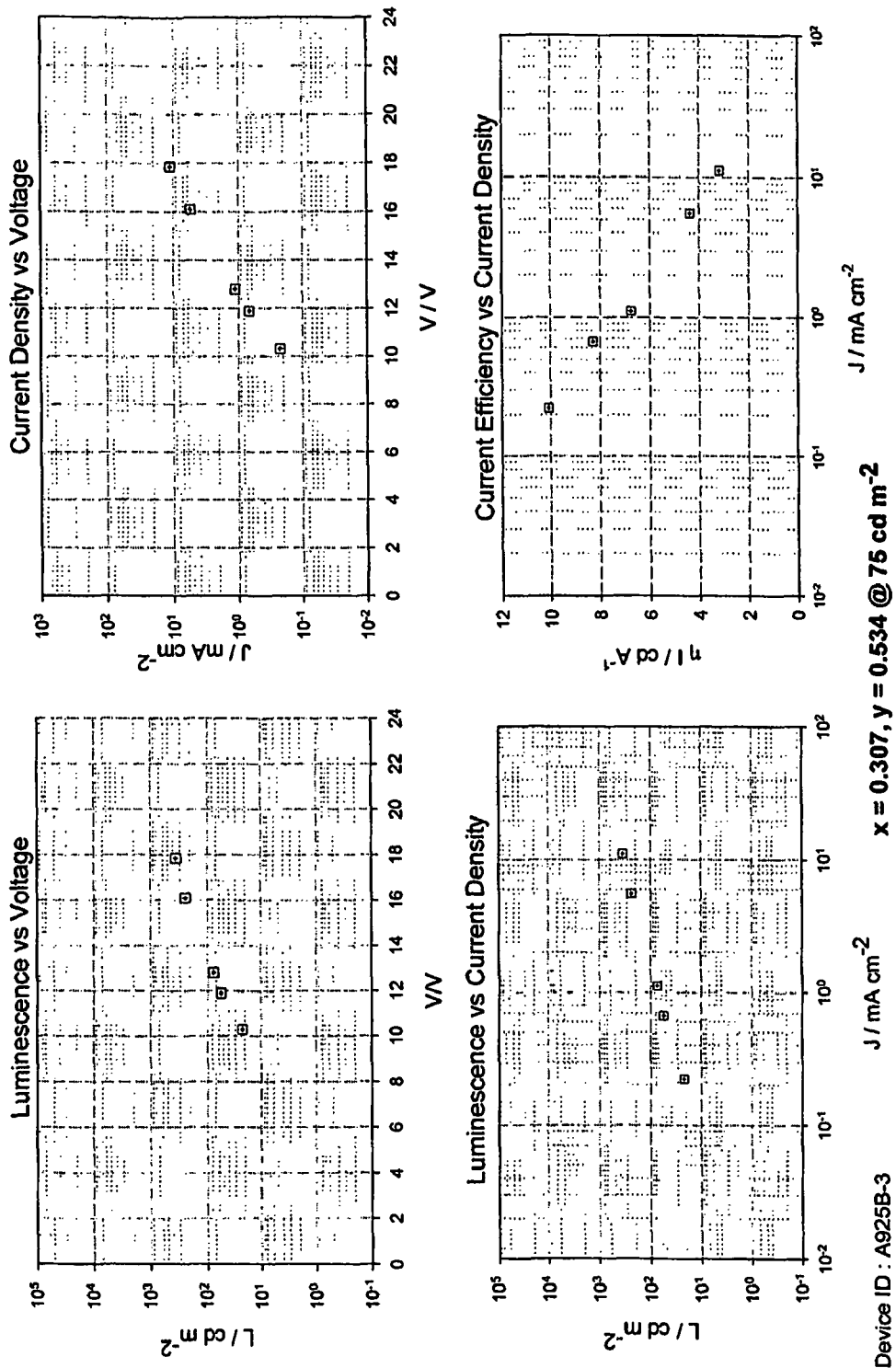
Figure 19:
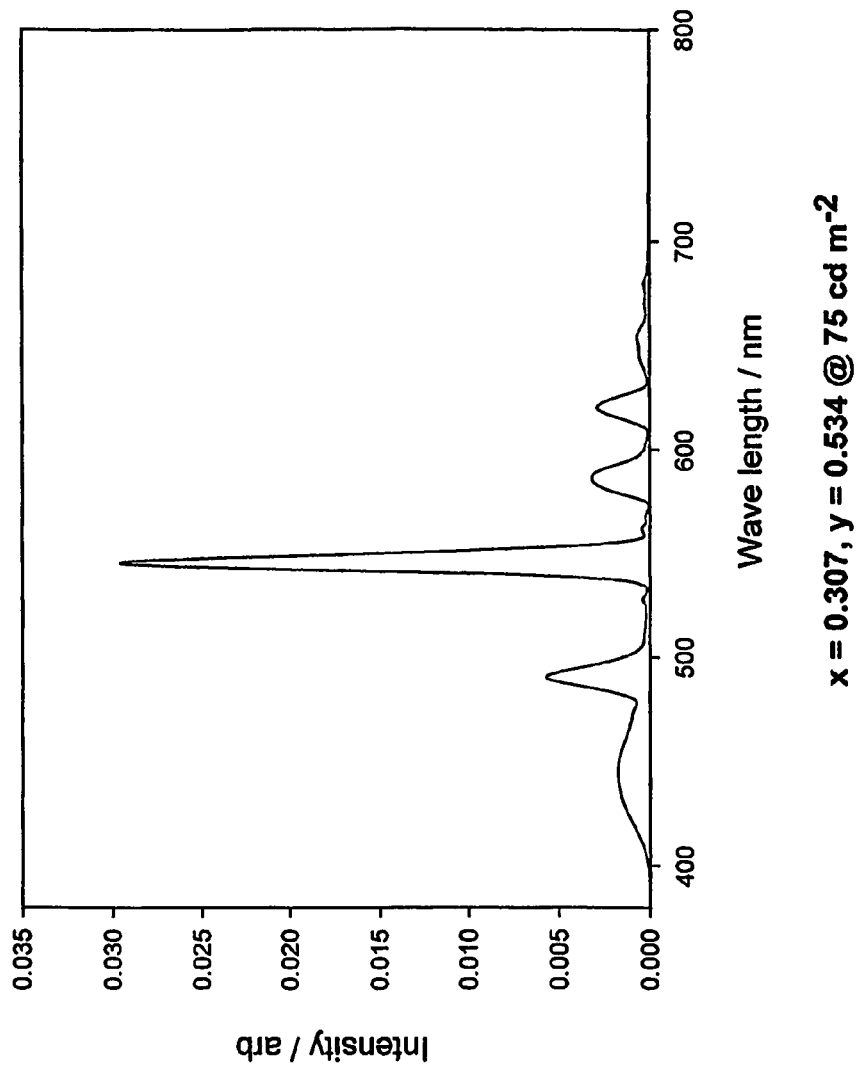
Figure 20:
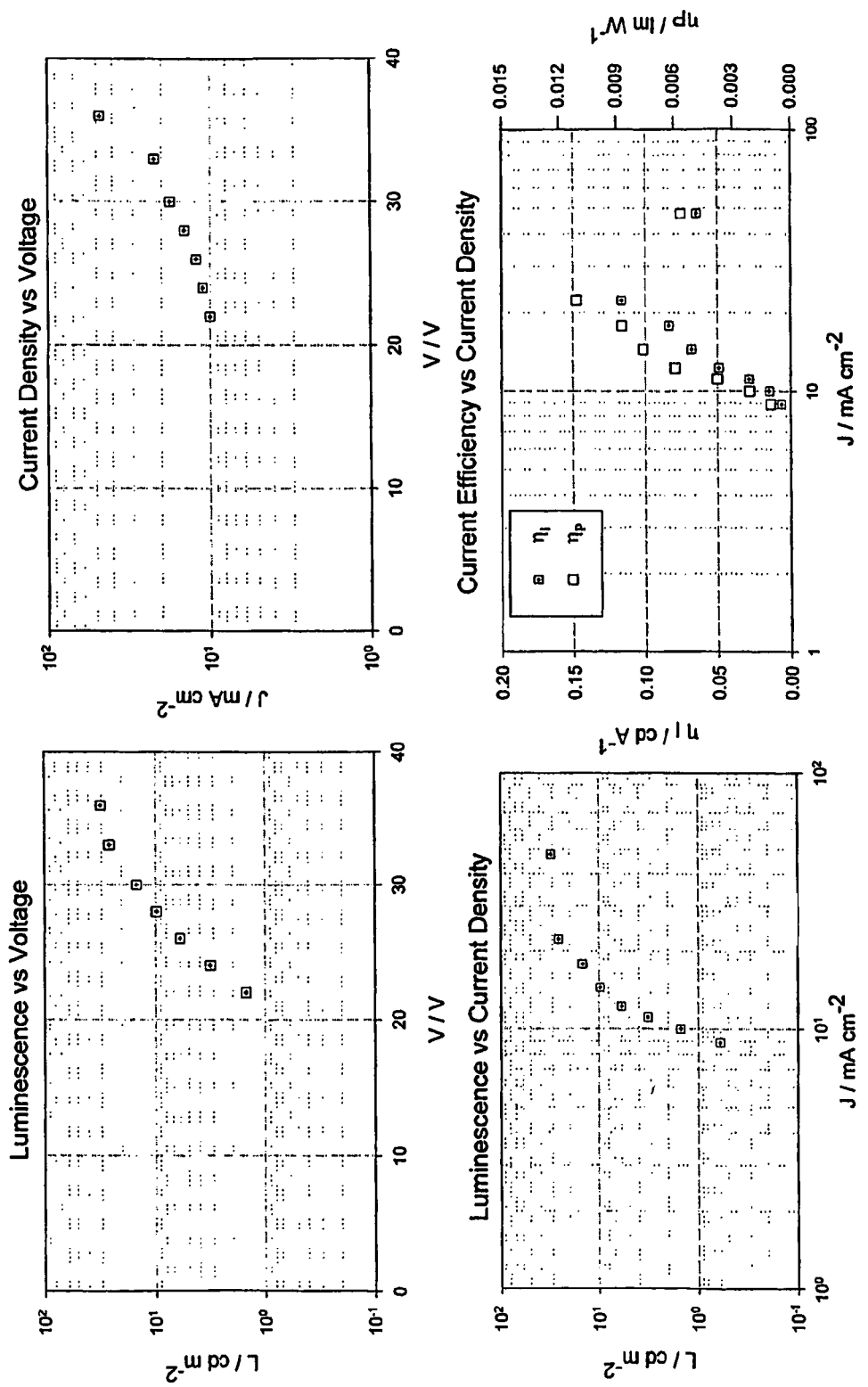
Figure 21:
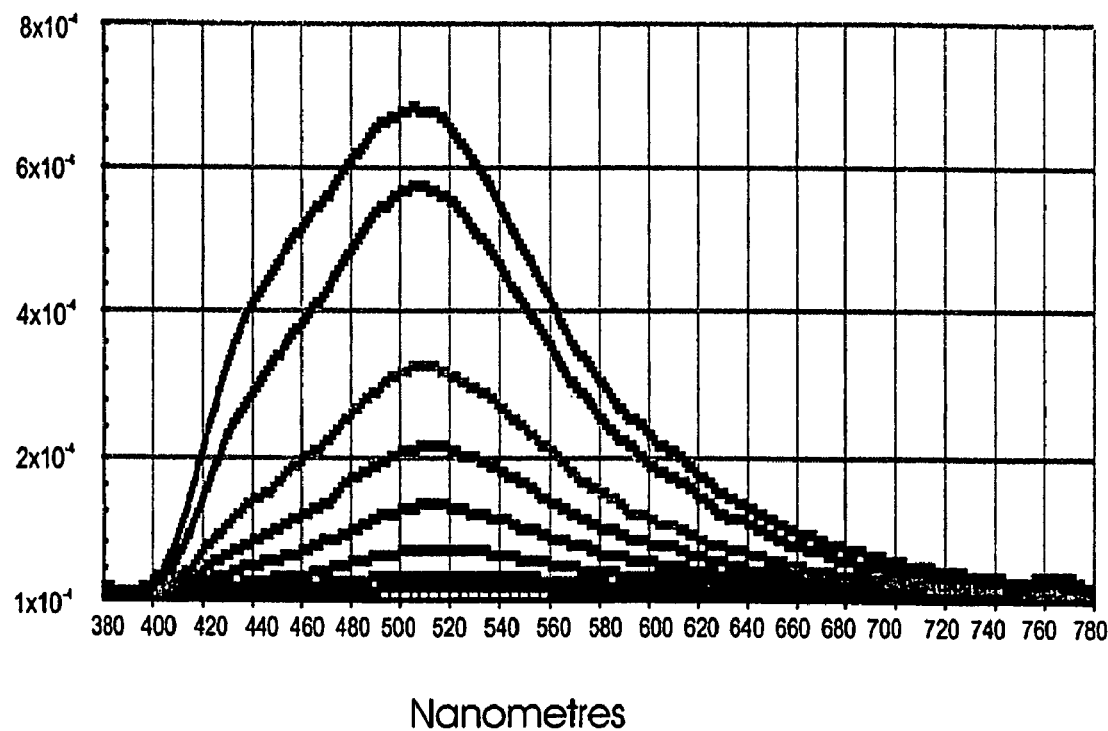
Figure 22:
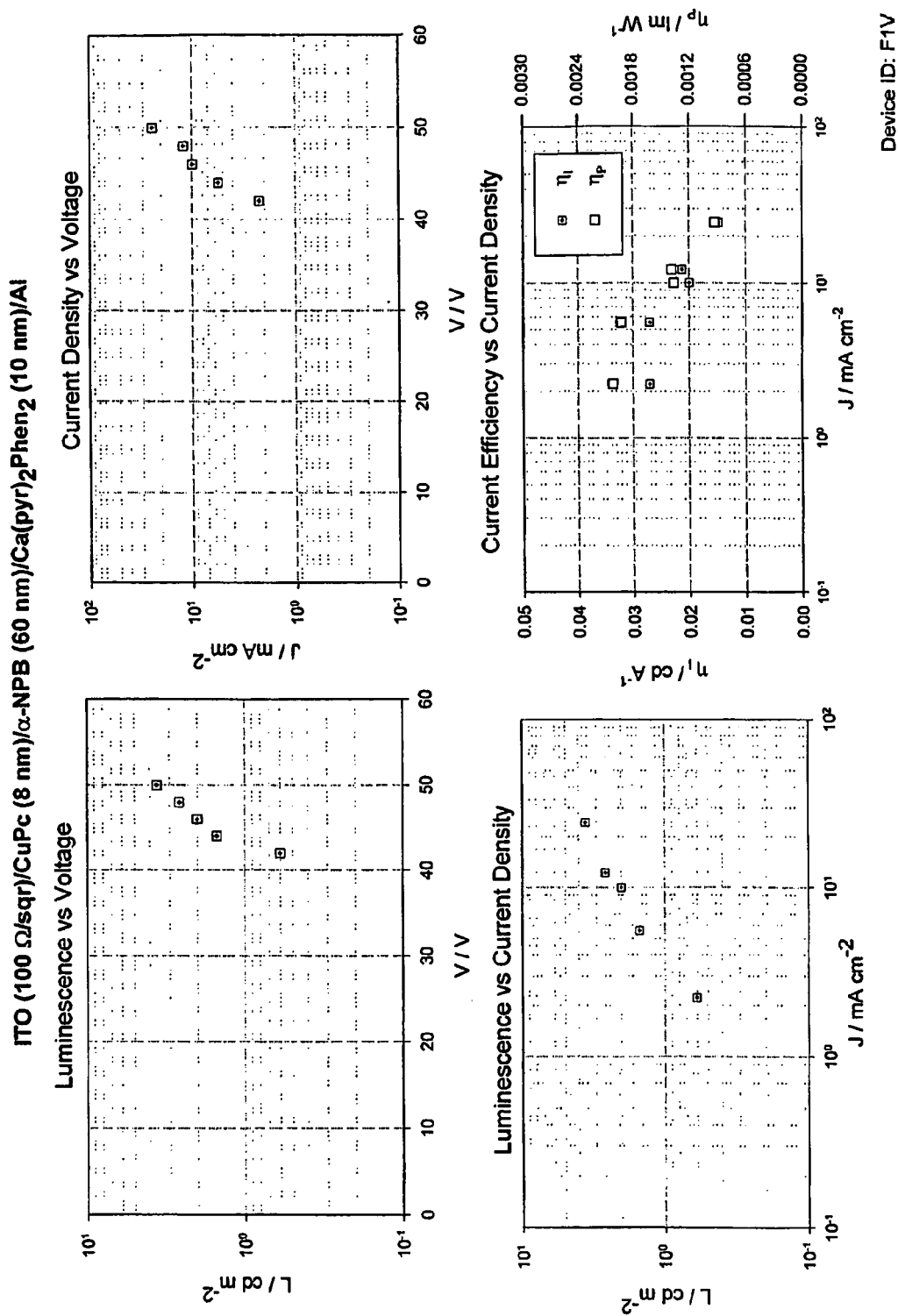
Figure 23:
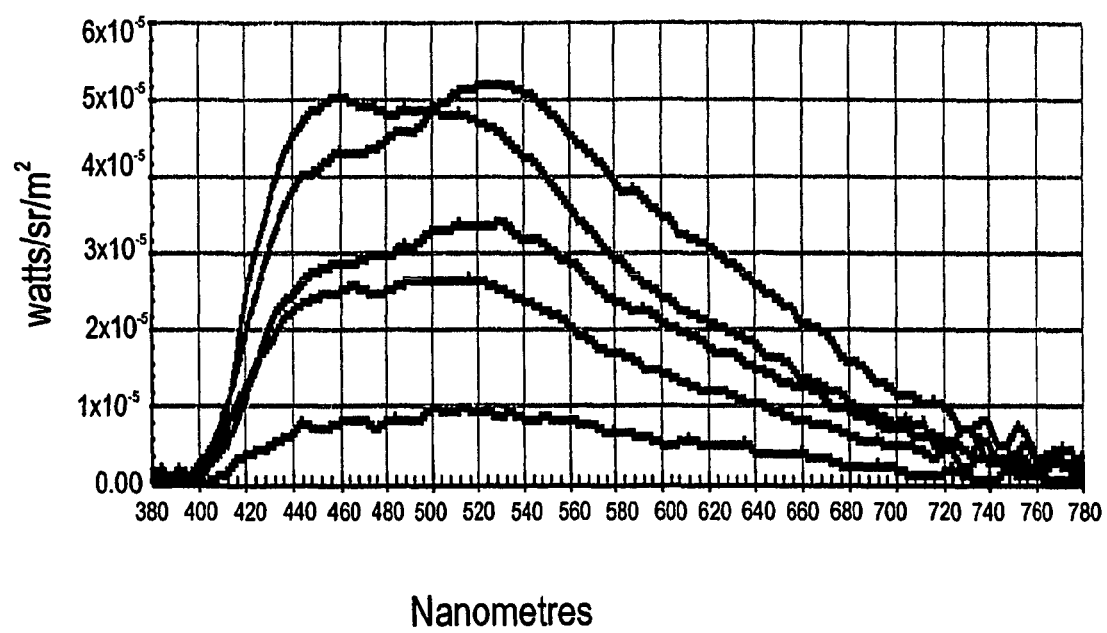

Other examples of $L_p$ chelates are as shown in FIG. 11 and fluorene and fluorene derivatives e.g. a shown in FIG. 12 and compounds of formulae as shown as shown in FIGS. 13 to 15.

The invention also provides an electroluminescent device comprising (i) a first electrode, (ii) an electroluminescent layer comprising a layer of a complex of formula (I) and (iii) a second electrode.

Examples of $R_1$ and/or $R_2$ and/or $R_3$ include aliphatic, aromatic and heterocyclic alkoxy, aryloxy and carboxy groups, substituted and substituted phenyl, fluorophenyl, biphenyl, phenanthrene, anthracene, naphthyl and fluorene groups alkyl groups such as t-butyl, heterocyclic groups such as carbazole.

Preferably $R_1$ and $R_2$ are $Ph_1$ and $Ph_2$ and at least one of $Ph_1$ and $Ph_2$ is a substituted or unsubstituted aromatic compound and the other Ph moiety is selected from hydrogen, and substituted and unsubstituted hydrocarbyl groups such as substituted and unsubstituted aliphatic groups, substituted and unsubstituted aromatic, heterocyclic and polycyclic ring structures, fluorocarbons such as trifluoryl methyl groups, halogens such as fluorine; substituted and unsubstituted fused aromatic, heterocyclic and polycyclic ring structures and can be copolymerisable with a monomer, e.g. styrene, fluorocarbons such as trifluoryl methyl groups, halogens such as fluorine. Examples include aliphatic, aromatic and heterocyclic alkoxy, aryloxy and carboxy groups, substituted and substituted phenyl, fluorophenyl, biphenyl, phenanthrene, anthracene, naphthyl and fluorene groups alkyl groups such as t-butyl, heterocyclic groups such as carbazole.

Preferably $R_1$ is methyl and $R_2$ is

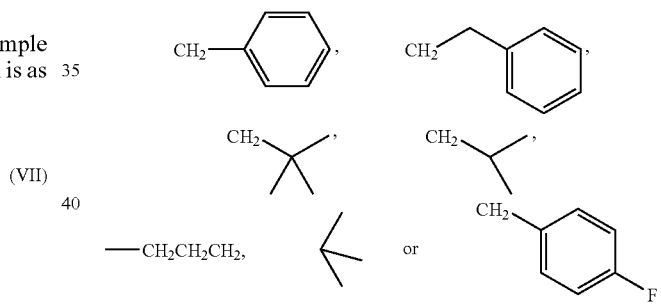

Preferred metals are metals other than aluminium, e.g. gallium, indium, germanium, tin (II), tin (IV), antimony (II), antimony (IV), lead (II), lead (IV) and metals of the first, second and third groups of transition metals in different valence states e.g. manganese, iron, ruthenium, osmium, cobalt, nickel, palladium(II), palladium(IV), platinum(II), platinum(IV), cadmium, chromium. titanium, vanadium, zirconium, tantulum, molybdenum, rhodium, iridium, titanium, niobium, scandium, yttrium, and $R_3$ is preferably a phenyl or substituted phenyl group.

Preferably there is a hole transmitting layer deposited on the transparent substrate and the electroluminescent material is deposited on the hole transmitting layer. The hole transmitting layer serves to transport holes and to block the electrons, thus preventing electrons from moving into the electrode without recombining with holes. The recombination of carriers therefore mainly takes place in the emitter layer.

Hole transmitting layers are used in small molecule based polymer electroluminescent devices and in electroluminescent devices based on rare earth metal complexes and any of the known hole transmitting materials in film form can be used.

Hole transmitting layers are used in polymer electroluminescent devices and any of the known hole transmitting materials in film form can be used.

The hole transmitting layer can be made of a film of an aromatic amine complex such as poly(vinylcarbazole), N,N'-diphenyl-N,N'-bis(3-methylphenyl)-1,1'-biphenyl-4,4'-diamine (TPD), an unsubstituted or substituted polymer of an amino substituted aromatic compound, a polyaniline, substituted polyanilines, polythiophenes, substituted polythiophenes, polysilanes etc. Examples of polyanilines are polymers of

(XI)

where R is in the ortho—or meta-position and is hydrogen, C1-18 alkyl, C1-6 alkoxy, amino, chloro, bromo, hydroxy or the group

where R is alky or aryl and R' is hydrogen, C1-6 alkyl or aryl with at least one other monomer of formula I above.

Polyanilines which can be used in the present invention have the general formula

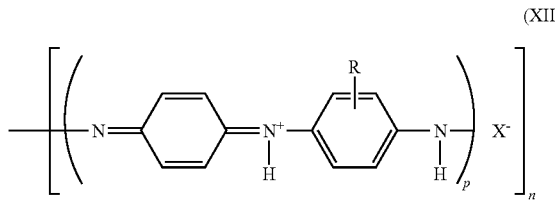
(XII)

where p is from 1 to 10 and n is from 1 to 20, R is as defined above and X is an anion, preferably selected from Cl, Br, SO$_4$, BF$_4$, PF$_6$, H$_2$PO$_3$, H$_2$PO$_4$, arylsulphonate, arenedicarboxylate, polystyrenesulphonate, polyacrylate alkysulphonate, vinylsulphonate, vinylbenzene sulphonate, cellulosesulphonate, camphor sulphonates, cellulose sulphate or a perfluorinated polyanion.

Examples of arylsulphonates are p-toluenesulphonate, benzenesulphonate, 9,10-anthraquinone-sulphonate and anthracenesulphonate, an example of an arenedicarboxylate is phthalate and an example of arenecarboxylate is benzoate.

We have found that protonated polymers of the unsubstituted or substituted polymer of an amino substituted aromatic compound such as a polyaniline are difficult to evaporate or cannot be evaporated; however we have surprisingly found that if the unsubstituted or substituted polymer of an amino substituted aromatic compound is de-protonated it can be easily evaporated i.e. the polymer is evaporable.

Preferably evaporable de-protonated polymers of unsubstituted or substituted polymer of an amino substituted aromatic compound are used. The de-protonated unsubstituted or substituted polymer of an amino substituted aromatic compound can be formed by deprotonating the polymer by treatment with an alkali such as ammonium hydroxide or an alkali metal hydroxide such as sodium hydroxide or potassium hydroxide.

The degree of protonation can be controlled by forming a protonated polyaniline and de-protonating. Methods of preparing polyanilines are described in the article by A. G. MacDiarmid and A. F. Epstein, Faraday Discussions, Chem Soc. 88 P 319 1989.

The conductivity of the polyaniline is dependent on the degree of protonation with the maximum conductivity being when the degree of protonation is between 40 and 60%, e.g. about 50%.

Preferably the polymer is substantially fully de-protonated.

A polyaniline can be formed of octamer units i.e. p is four, e.g.

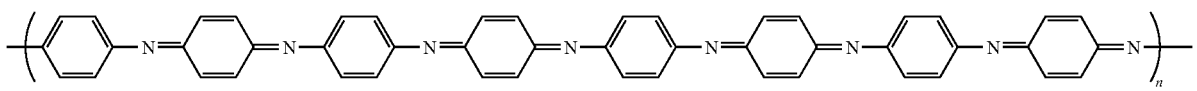

The polyanilines can have conductivities of the order of 1×10$^{-1}$ Siemen cm$^{-1}$ or higher.

The aromatic rings can be unsubstituted or substituted, e.g. by a C1 to 20 alkyl group such as ethyl.

The polyaniline can be a copolymer of aniline and preferred copolymers are the copolymers of aniline with o-anisidine, m-sulphanilic acid or o-aminophenol, or o-toluidine with o-aminophenol, o-ethylaniline, o-phenylene diamine or with amino anthracenes.

Other polymers of an amino substituted aromatic compound which can be used include substituted or unsubstituted polyaminonapthalenes, polyaminoanthracenes, polyaminophenaiithrenes, etc. and polymers of any other condensed polyaromatic compound. Polyaminoanthracenes and methods of making them are disclosed in U.S. Pat. No. 6,153,726. The aromatic rings can be unsubstituted or substituted, e.g. by a group R as defined above.

The polyanilines can be deposited on the first electrode by conventional methods, e.g. by vacuum evaporation, spin coating, chemical deposition, direct electrodeposition etc. Preferably the thickness of the polyaniline layer is such that the layer is conductive and transparent and is preferably from 20 nm to 200 nm. The polyanilines can be doped or undoped. When they are doped they can be dissolved in a solvent and deposited as a film, when they are undoped they are solids and can be deposited by vacuum evaporation i.e. by sublimation.

The structural formulae of some other hole transmitting materials are shown in FIGS. 1, 2, 3, 4 and 5 of the drawings, where R, $R_1$, $R_2$ and $R_3$ can be the same or different and are selected from hydrogen, and substituted and unsubstituted hydrocarbyl groups such as substituted and unsubstituted aliphatic groups, substituted and unsubstituted aromatic, heterocyclic and polycyclic ring structures, fluorocarbons such as trifluoryl methyl groups, halogens such as fluorine or thiophenyl groups; $R_1$, $R_2$ and $R_3$ can also form substituted and unsubstituted fused aromatic, heterocyclic and polycyclic ring structures and can be copolymerisable with a monomer, e.g. styrene. X is Se, S or O, Y can be hydrogen, substituted or unsubstituted hydrocarbyl groups, such as substituted and unsubstituted aromatic, heterocyclic and polycyclic ring structures, fluorine, fluorocarbons such as trifluoryl methyl groups, halogens such as fluorine or thiophenyl groups or nitrile.

Examples of $R_1$ and/or $R_2$ and/or $R_3$ include aliphatic, aromatic and heterocyclic alkoxy, aryloxy and carboxy groups, substituted and substituted phenyl, fluorophenyl, biphenyl, phenanthrene, anthracene, naphthyl and fluorene groups alkyl groups such as t-butyl, heterocyclic groups such as carbazole.

The hole transporting material can optionally be mixed with the electroluminescent material in a ratio of 5-95% of the electroluminescent material to 95 to 5% of the hole transporting compound.

Other hole transporting materials which can be used are conjugated polymers.

U.S. Pat. No. 5,807,627 discloses an electroluminescence device in which there are conjugated polymers in the electroluminescent layer. The conjugated polymers referred to are defined as polymers for which the main chain is either fully conjugated possessing extended pi molecular orbitals along the length of the chain or else is substantially conjugated, but with interruptions to conjugation, either random or regular along the main chain. They can be homopolymers or copolymers.

The conjugated polymer used can be any of the conjugated polymers disclosed or referred to in U.S. Pat. No. 5,807,627, PCT/WO90/13148 and PCT/WO92/03490.

The conjugated polymers disclosed are poly(p-phenylenevinylene)-PPV and copolymers including PPV. Other preferred polymers are poly(2,5 dialkoxyphenylene vinylene) such as poly(2-methoxy-5-(2-methoxypentyloxy-1,4-phenylene vinylene), poly(2-methoxypentyloxy)-1,4-phenylenevinylene), poly(2-methoxy-5-(2-dodecyloxy-1,4-phenylenevinylene) and other poly(2,5 dialkoxyplhenylenevinylenes) with at least one of the alkoxy groups being a long chain solubilising alkoxy group, poly fluorenes and oligofluorenes, polyphenylenes and oligophenylenes, polyanthracenes and oligo anthracenes, polythiophenes and oligothiophenes.

In PPV the phenylene ring may optionally carry one or more substituents, e.g. each independently selected from alkyl, preferably methyl, alkoxy, preferably methoxy or ethoxy.

Any poly(arylenevinylene) including substituted derivatives thereof can be used and the phenylene ring in poly(p-phenylenevinylene) may be replaced by a fused ring system such as anthracene or naphthlyene ring and the number of vinylene groups in each polyphenylenevinylene moeity can be increased, e.g. up to 7 or higher.

The conjugated polymers can be made by the methods disclosed in U.S. Pat. No. 5,807,627, PCT/WO90/13148 and PCT/WO92/03490.

The hole transmitting material and the light emitting metal compound can be mixed to form one layer, e.g. in an proportion of 5 to 95% of the hole transmitting material to 95 to 5% of the light emitting metal compound.

Figure 1:
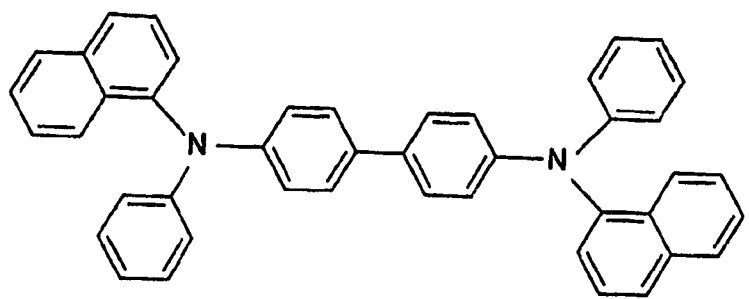
FIGS. 1-5 are formulae drawings for hole transmitting materials in accordance with this invention.
Figure 1:
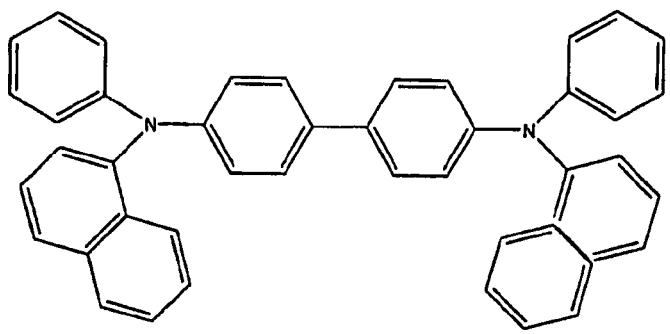
Figure 1:
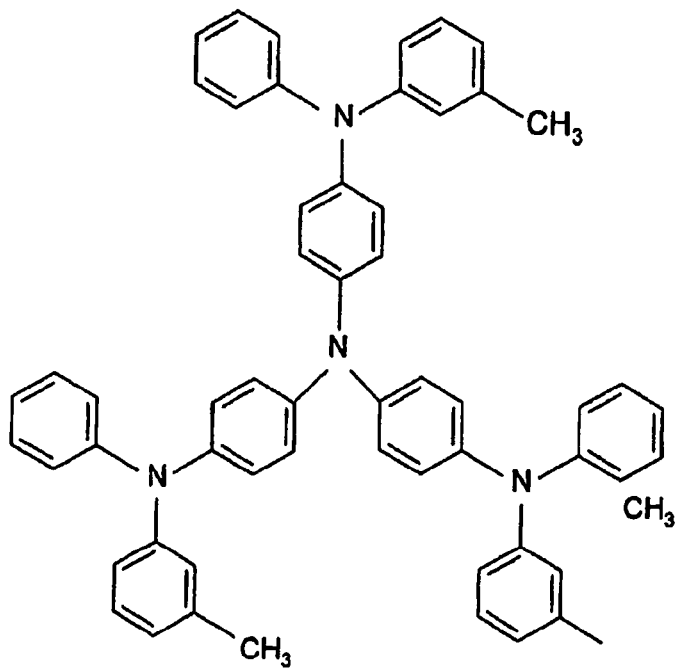
Figure 2:
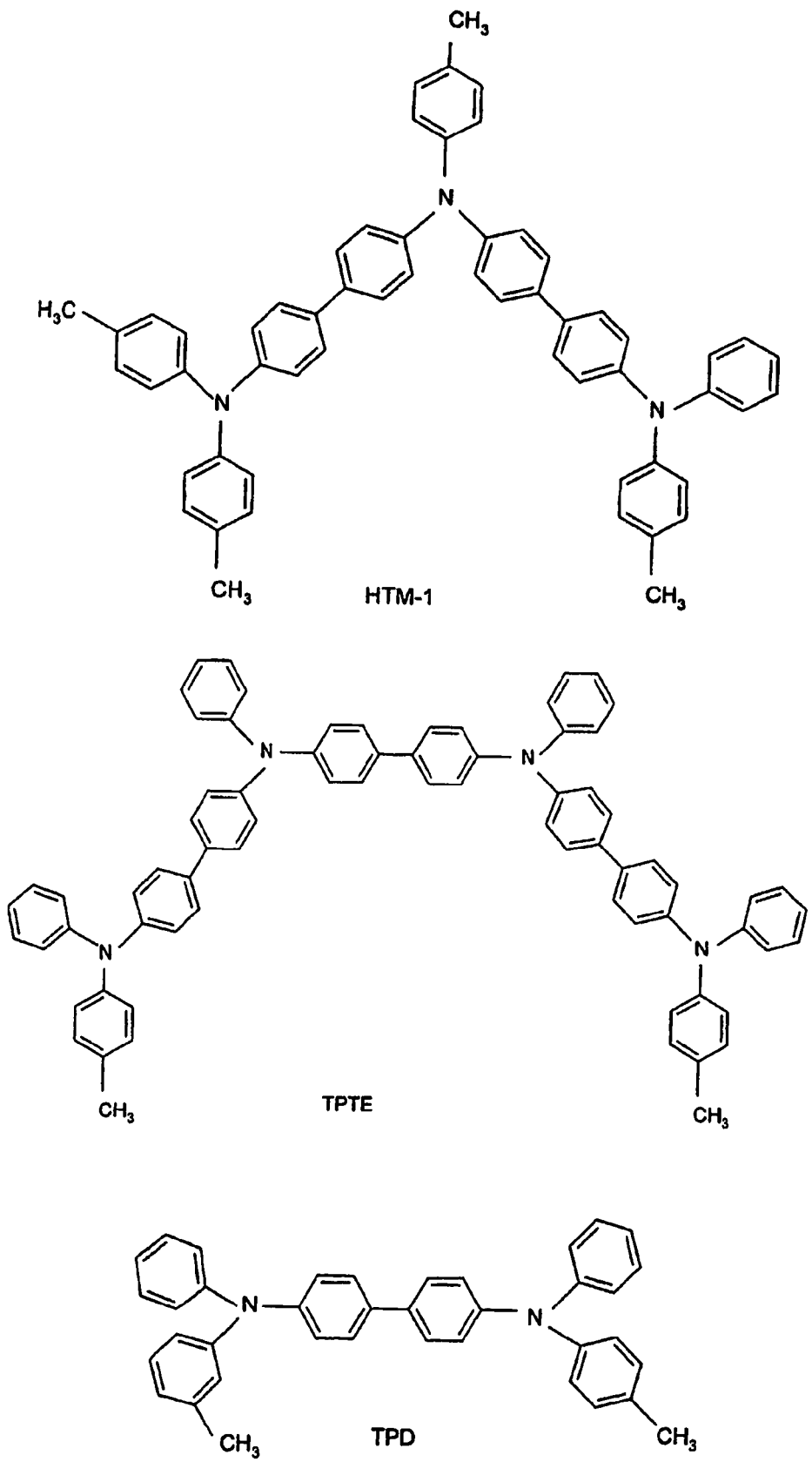
Figure 3:
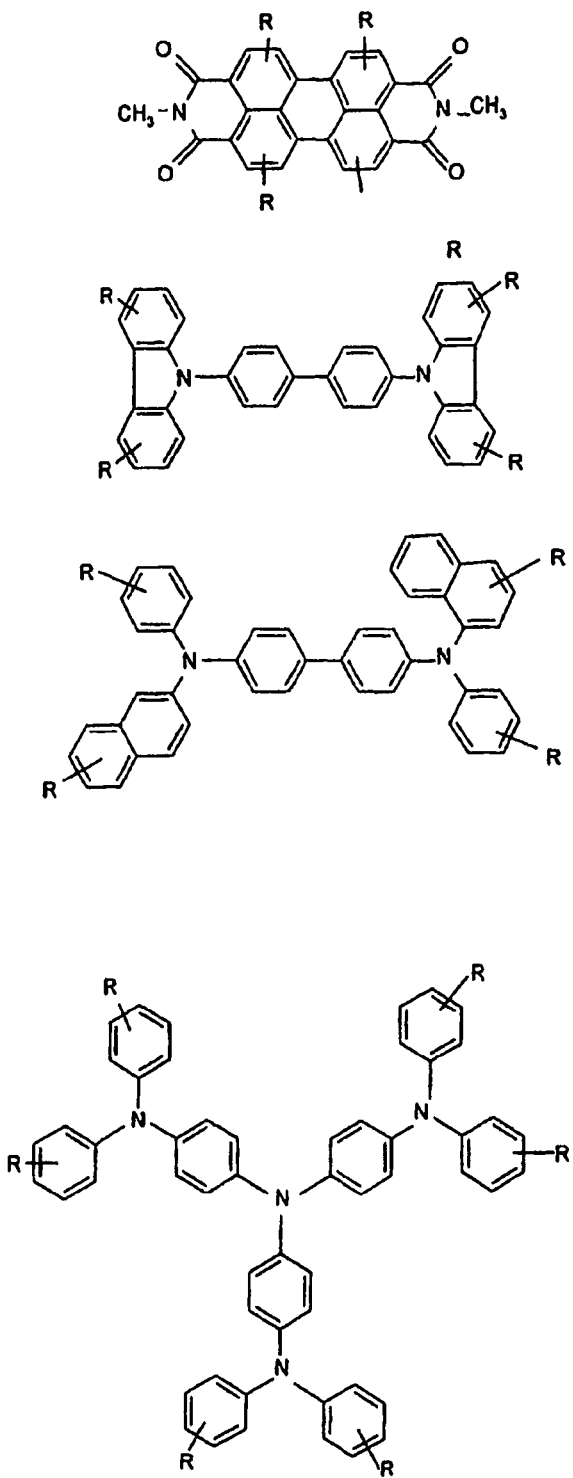
Figure 4:
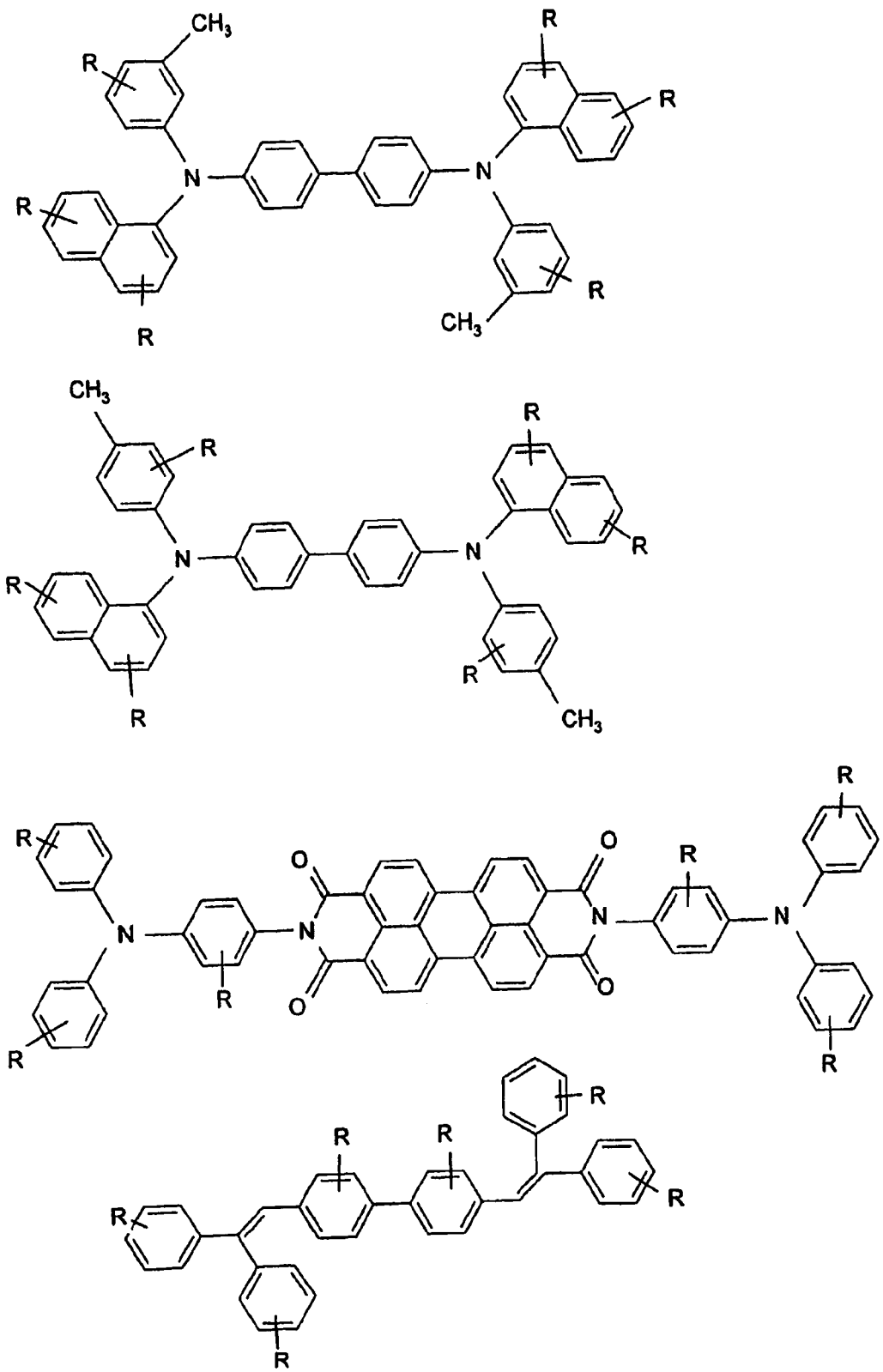
Figure 5:
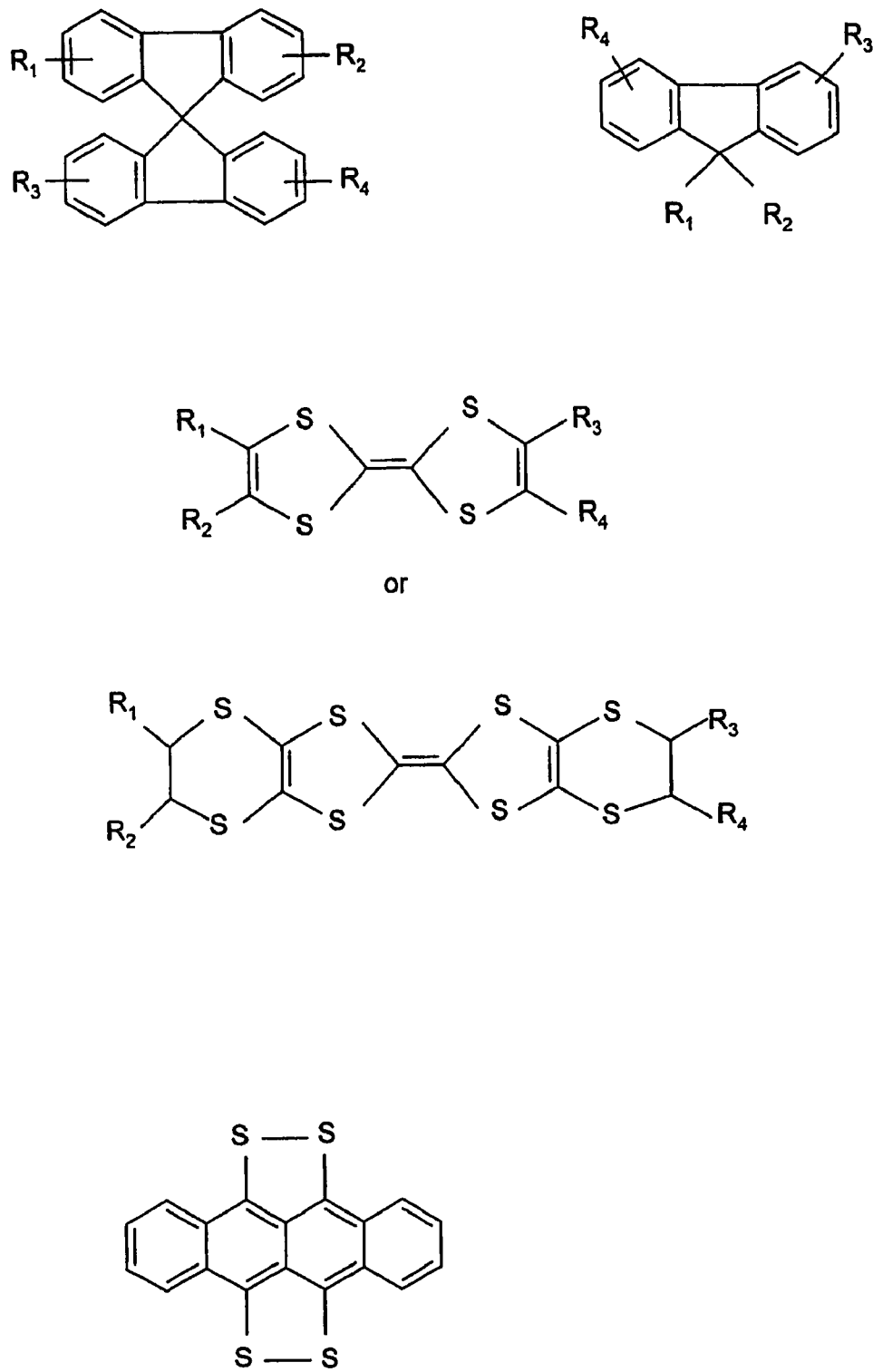
Figure 6:
FIGS. 6 and 7 are formulae drawings of electron transmitting materials in accordance with this invention.
Figure 6:
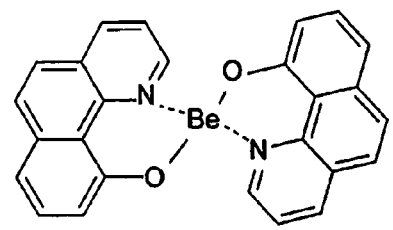
Figure 6:
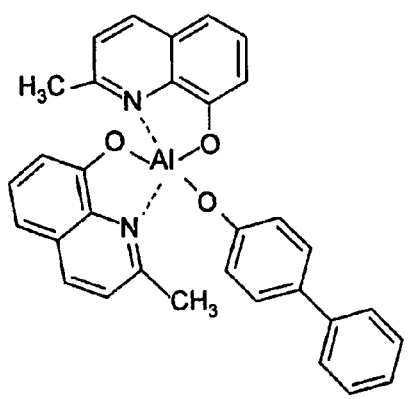
Figure 6:
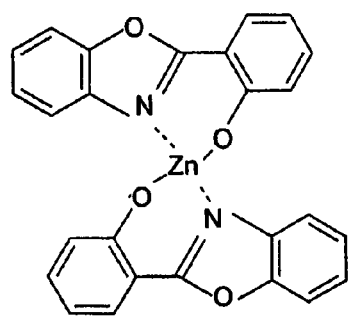
Figure 6:
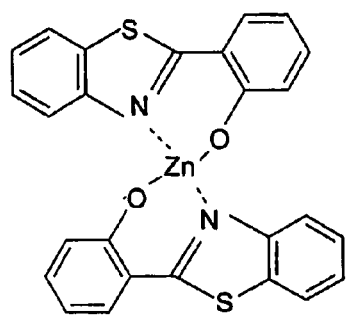
Figure 6:
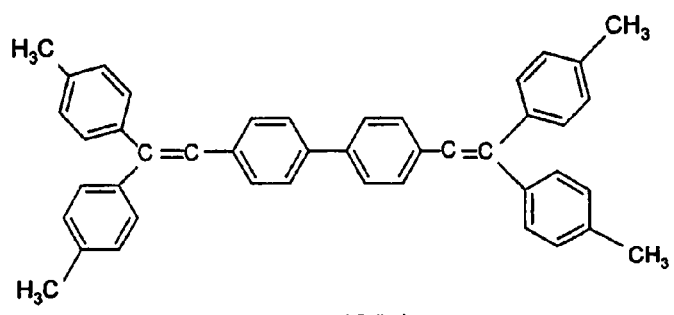
Figure 7:
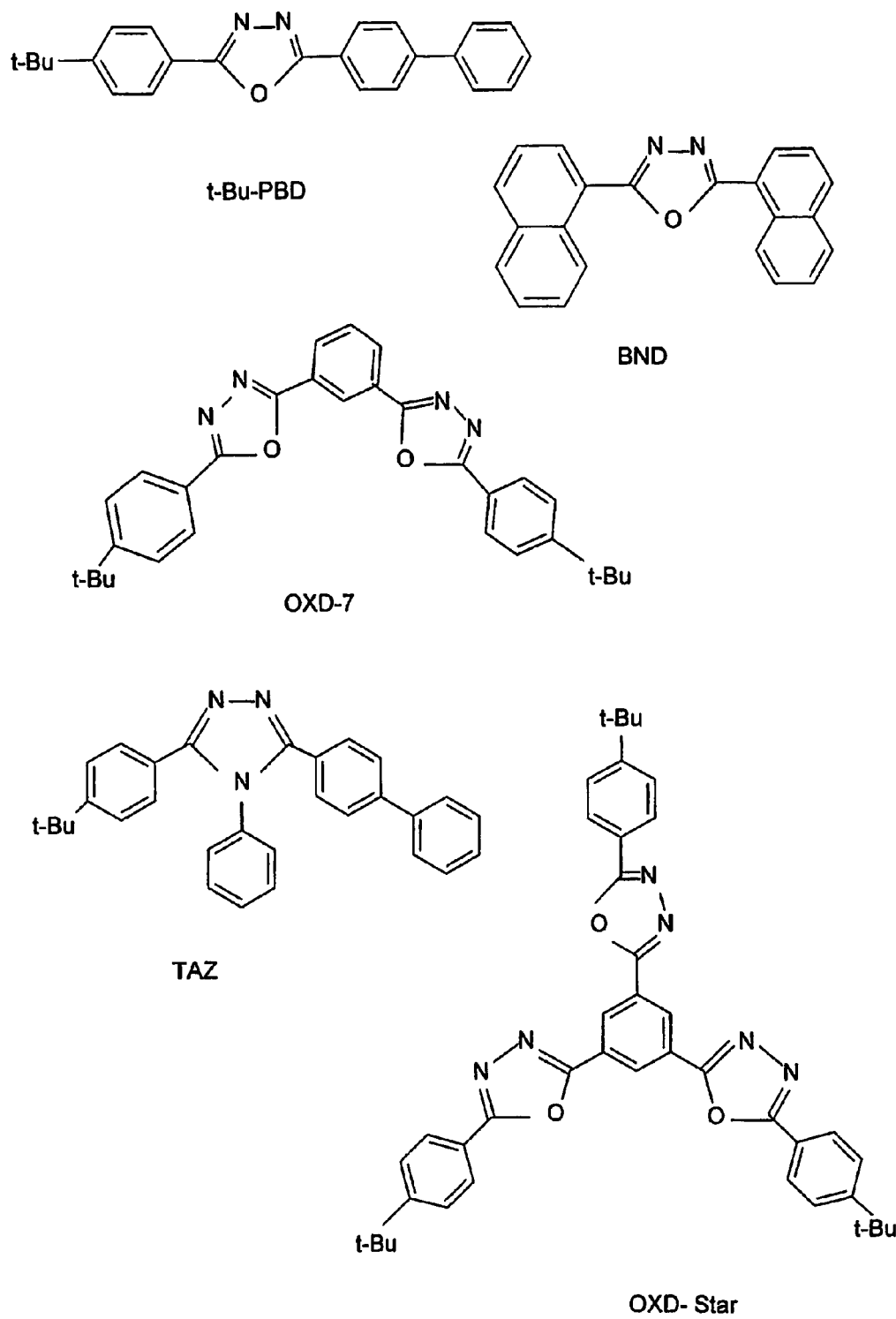

Optionally there is a layer of an electron transmitting material between the cathode and the electroluminescent material layer. The electron transmitting material is a material which will transport electrons when an electric current is passed through it. Electron transmitting materials include a metal complex such as a metal quinolate, e.g. an aluminium quinolate, lithium quinolate, a cyano anthracene such as 9,10 dicyano anthracene, a polystyrene sulphonate and compounds of formulae shown in FIGS. 6 and 7. Instead of being a separate layer the electron transmitting material can be mixed with the electroluminescent material to form one layer, e.g. in a proportion of 5 to 95% of the electron transmitting material to 95 to 5% of the light emitting metal compound.

The electroluminescent layer can comprise a mixture of the light emitting metal compound with the hole transmitting material and electron transmitting material.

The electroluminescent material can be deposited on the substrate directly by vacuum evaporation or evaporation from a solution in an organic solvent. The solvent which is used will depend on the material but chlorinated hydrocarbons such as dichloromethane and n-methyl pyrrolidone; dimethyl sulphoxide; tetra hydrofuran; dimethylformamide etc. are suitable in many cases.

Alternatively electroluminescent material can be deposited by spin coating from solution, or by vacuum deposition from the solid state, e.g. by sputtering, or any other conventional method can be used.

Preferably the first electrode is a transparent substrate such as a conductive glass or plastic material which acts as the anode. Preferred substrates are conductive glasses such as indium tin oxide coated glass, but any glass which is conductive or has a transparent conductive layer such as a metal or conductive polymer can be used.

Conductive polymers and conductive polymer coated glass or plastics materials can also be used as the substrate.

The second electrode functions as the cathode and can be any low work function metal, e.g. aluminium, calcium, lithium, silver/magnesium alloys etc; aluminium is a preferred metal.

The display of the invention may be monochromatic or polychromatic. Electroluminescent rare earth chelate compounds are known which will emit a range of colours, e.g. red, green, and blue light and white light and examples are disclosed in Patent Applications WO98/58037 PCT/GB98/01773, PCT/GB99/03619, PCT/GB99/04030, PCT/GB99/04024, PCT/GB99/04028, PCT/GB00/00268 and can be used to form OLEDs emitting those colours. Thus, a full colour display can be formed by arranging three individual backplanes, each emitting a different primary monochrome colour, on different sides of an optical system, from another side of which a combined colour image can be viewed. Alternatively, rare earth chelate electroluminescent compounds emitting different colours can be fabricated so that adjacent diode pixels in groups of three neighbouring pixels produce red, green and blue light. In a further alternative, field sequential colour filters can be fitted to a white light emitting display.

Either or both electrodes can be formed of silicon and the electroluminescent material and intervening layers of a hole transporting and electron transporting materials can be formed as pixels on the silicon substrate. Preferably each pixel comprises at least one layer of a rare earth chelate electroluminescent material and an (at least semi-) transparent electrode in contact with the organic layer on a side thereof remote from the substrate.

Preferably, the substrate is of crystalline silicon and the surface of the substrate may be polished or smoothed to produce a flat surface prior to the deposition of electrode, or electroluminescent compound. Alternatively a non-planarised silicon substrate can be coated with a layer of conducting polymer to provide a smooth, flat surface prior to deposition of further materials.

In one embodiment, each pixel comprises a metal electrode in contact with the substrate. Depending on the relative work functions of the metal and transparent electrodes, either may serve as the anode with the other constituting the cathode.

When the silicon substrate is the cathode an indium tin oxide coated glass can act as the anode and light is emitted through the anode. When the silicon substrate acts as the anode, the cathode can be formed of a transparent electrode which has a suitable work function, for example by a indium zinc oxide coated glass in which the indium zinc oxide has a low work function. The anode can have a transparent coating of a metal formed on it to give a suitable work function. These devices are sometimes referred to as top emitting devices or back emitting devices.

The metal electrode may consist of a plurality of metal layers, for example a higher work function metal such as aluminium deposited on the substrate and a lower work function metal such as calcium deposited on the higher work function metal. In another example, a further layer of conducting polymer lies on top of a stable metal such as aluminium.

Preferably, the electrode also acts as a mirror behind each pixel and is either deposited on, or sunk into, the planarised surface of the substrate. However, there may alternatively be a light absorbing black layer adjacent to the substrate.

In still another embodiment, selective regions of a bottom conducting polymer layer are made non-conducting by exposure to a suitable aqueous solution allowing formation of arrays of conducting pixel pads which serve as the bottom contacts of the pixel electrodes.

As described in WO00/60669 the brightness of light emitted from each pixel is preferably controllable in an analogue manner by adjusting the voltage or current applied by the matrix circuitry or by inputting a digital signal which is converted to an analogue signal in each pixel circuit. The substrate preferably also provides data drivers, data converters and scan drivers for processing information to address the array of pixels so as to create images. When an electroluminescent material is used which emits light of a different colour, depending on the applied voltage, the colour of each pixel can be controlled by the matrix circuitry.

In one embodiment, each pixel is controlled by a switch comprising a voltage controlled element and a variable resistance element, both of which are conveniently formed by metal-oxide-semiconductor field effect transistors (MOSFETs) or by an active matrix transistor.

The invention is illustrated in the examples.

Example 1

Preparation of Tris-(4-$^t$Butylacetyl-3-methyl-1-phenyl-pyrazol-5-onato)Gallium (Ga($^t$BuPz)$_3$

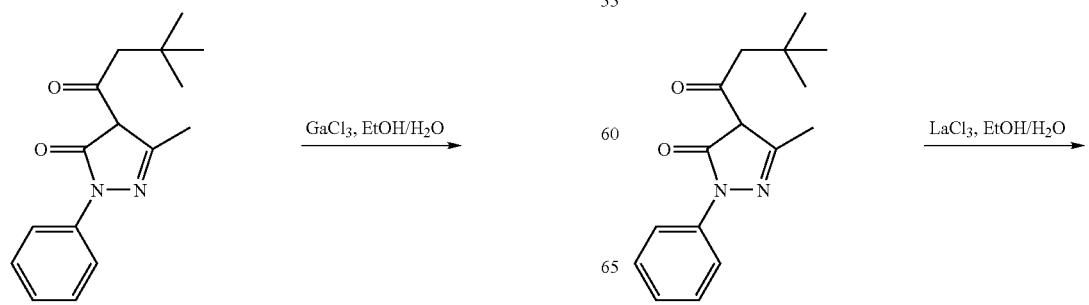

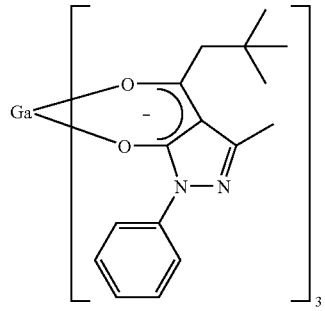

4-$^t$Butylacetyl-3-methyl-1-phenyl-pyrazol-5-one (2.83 g. 10.39 mmol), in a 100 ml round bottom flask, was dissolved in ethanol (~50 mL) with gentle heating. Gallium(III) chloride (0.61 g, 3.46 mmol) was dissolved in H$_2$O (~10 mL) and added to the pyrazolone solution. The resulting suspension was heated to reflux for 2 hours and then allowed to cool. The resulting suspension was filtered and washed with H$_2$O (3×10 ml) and EtOH (3×10 ml) then dried under vacuum at 80° C. to give a pink powder with the following analysis.

| Ga($^t$BuPz)$_3$ | C | H | N |
|---|---|---|---|
| Theoretical | 65.24 | 6.50 | 9.51 |
| Found | 65.07 | 6.57 | 9.46 |

Melting point: 252.1° C. (D.S.C.)
Emission $\lambda_{max}$: ~450 nm
Photoluminescence Efficiency (x,y): 0.001 cdm$^2$ μW$^{-1}$ (0.21, 0.24)

PL Measurement:
  PL spectra was measured by Lot Oriel Multispec Model 77400 CCD Camera.
  The measurement was carried out from the powder by spreading the powder on a spectrosil plate.
  Reagents Gallium(III) chloride, anhydrous, 99.99%; Aldrich; 45,089-8
4-$^t$Butylac~tyl-3-methyl-1-phenyl-pyrazol-5-onato as prepared Ethanol, denatured with 4.8% Methanol; Fluka; 02857

Example 2

Preparation of Tris-(4-tButylacetyl-3-methyl-1-phenyl-pyrazol-5-onato)Lanthanum (La($^t$BuPz)$_3$

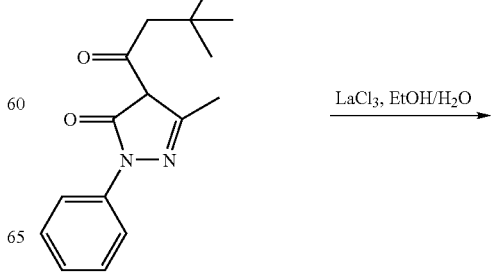

-continued

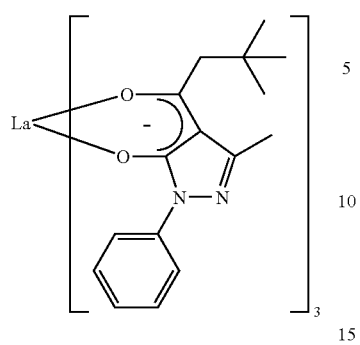

4-'Butylacetyl-3-methyl-1-phenyl-pyrazol-5-one (2.93 g, 10.76 mmol), in a 100 ml round bottom flask, was dissolved in ethanol (~50 mL) with gentle heating. Lanthanum(III) chloride (1.27 g, 3.59 mmol) was dissolved in $H_2O$ (~10 mL) and added to the pyrazolone solution. The resulting suspension was heated to reflux for 2 hours and then allowed to cool. The resulting suspension was filtered and washed with $H_2O$ (3×10 mL) and EtOH (3×10 mL) then dried under vacuum at 80° C. to give a white powder with the following analysis.

| Sc('BuPz)$_3$ | C | H | N |
|---|---|---|---|
| Theoretical | 60.48 | 6.03 | 8.82 |
| Found | 59.92 | 6.28 | 8.67 |

Melting point: 114.1° C. ($T_g$)

Emission λmax.: 441.8 nm

Photoluminescence Efficiency (x,y): 0.003 cdm$^2$ μW$^{-1}$ (0.20, 0.22)

Reagents

Lanthanum(III) chloride hexahydrate, 99.9%; Strem Chmeicals, 93-5731; Lot no. 251194-S 4-'Butylacetyl-3-methyl-1-phenyl-pyrazol-5-one as prepared Ethanol, denatured with 4.8% Methanol; Fluka; 02857.

Example 3

Preparation of Tri-(4-'Butylacetyl-3-methyl-phenyl-pyrazol-5-onato)Scandium (Sc('BuPz)$_3$

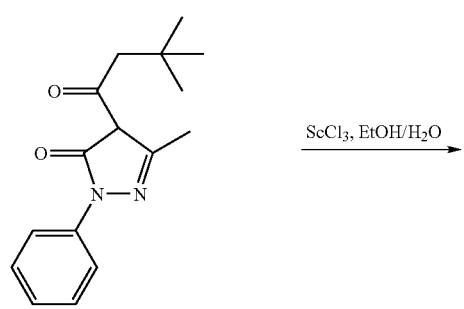

-continued

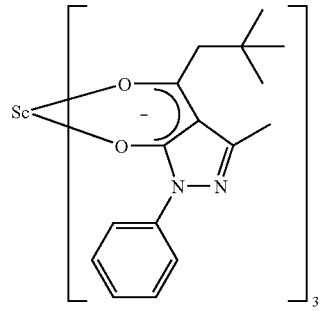

4-'Butylacetyl-3-methyl-1-phenyl-pyrazol-5-one (1.07 g. 3.93 mmol), in a 100 ml round bottom flask, was dissolved in ethanol (—50 mL) with gentle heating. Scandium(III) chloride hexahydrate (0.34 g. 1.31 mmol) was dissolved in $H_2O$ (~40 mL) and added to the pyrazolone solution. The resulting suspension was heated to reflux for 2 hours and then allowed to cool. The resulting suspension was filtered and washed with $H_2O$ (3×10 ml,) and EtOH (3×10 ml) then dried under vacuum at 80° C. to give a white powder with the following analysis.

| Sc('BuPz)$_3$ | C | H | N |
|---|---|---|---|
| Theoretical | 67.12 | 6.69 | 9.78 |
| Found | 66.73 | 6.65 | 9.62 |

Melting point: 275.5° C. (D.S.C.)

Emission Max.: 448.55 nm

Photoluminescence Efficiency (x,y): 0.004 cdm$^2$ μW$^{-1}$ (0.22, 0.28)

Reagents

Scandium(III) chloride hexahydrate, 99.9%; Strem Chemicals; 93-2111, Lot no. B4745091

4-'Butylacetyl-3-methyl-1-phenyl-pyrazol-5-one as prepared

Ethanol, denatured with 4.8% Methanol; Fluka; 02857

Example 4

Preparation of Tris-(4-'Butylacetyl-3-methyl-1-phenyl-pyrazol-5-onato)Terbium (Tb('BuPz)$_3$

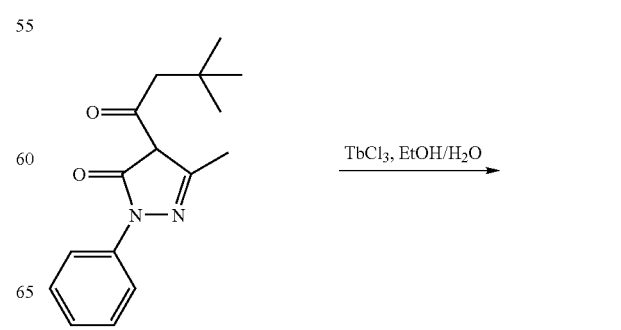

-continued

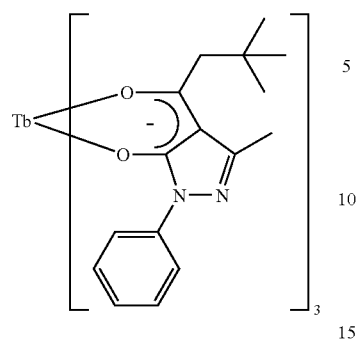

4-<sup>t</sup>Butylacetyl-3-methyl-1-phenyl-pyrazol-5-one (1.45 g, 5.32 mmol), in a 100 ml round bottom flask, was dissolved in ethanol (~50 mL) with gentle heating. Terbium(III) chloride hexahydrate (0.66 g, 1.77 mmol) was dissolved in $H_2O$ (~10 mL) and added to the pyrazolone solution. The resulting suspension was heated to reflux for 2 hours and then allowed to cool. The resulting suspension was filtered and washed with $H_2O$ (3×10 mL) and EtOH (3×10 mL) then dried under vacuum at 80° C. to give a white powder with the following analysis.

| Tb($^t$BuPz)$_3$ | C | H | N |
|---|---|---|---|
| Theoretical | 59.24 | 5.91 | 8.64 |
| Found | 59.86 | 6.23 | 8.75 |

Melting point: 252.6° C. (D.S.C.)

Emission Max.: 492.4 nm, 547.6 nm

Photoluminescence Efficiency (x,y): cdm$^2$ μW$^{-1}$

Reagents

Terbium(III) chloride, 99.9%; Acros

4-<sup>t</sup>Butylacetyl-3-methyl-1-phenyl-pyrazol-5-one as prepared

Ethanol, denatured with 4.8% Methanol; Fluka; 02857

Example 5

Preparation of Tetrakis-(4-<sup>t</sup>Butylacetyl-3-methyl-1-phenyl-pyrazol-5-onato)Thorium (Th($^t$BuPz)$_3$

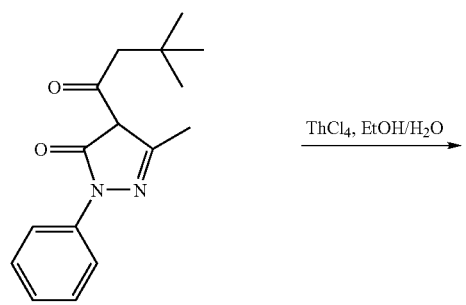

-continued

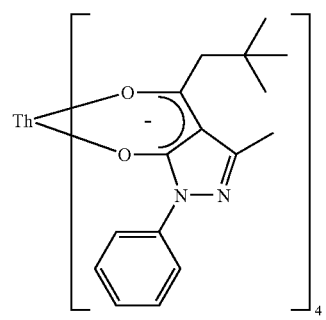

4-<sup>t</sup>Butylacetyl-3-methyl-1-phenyl-pyrazol-5-one (1.92 g. 7.06 mmol), in a 100 ml round bottom flask, was dissolved in ethanol (~50 mL) with gentle heating. Thorium(IV) chloride hexahydrate (0.66 g. 1.77 mmol) was dissolved in $H_2O$ (~10 mL) and added to the pyrazolone solution. The resulting suspension was heated to reflux for 2 hours and then allowed to cool. The resulting suspension was filtered and washed with $H_2O$ (3×10 ml) and EtOH (3×10 mL) then dried under vacuum at 80° C. to give a pink powder with the following analysis.

| Th($^t$BuPz)$_4$ | C | H | N |
|---|---|---|---|
| Theoretical | 58.35 | 5.81 | 8.58 |
| Found | 58.49 | 6.06 | 8.32 |

Melting point: 254.7° C. (D.S.C.)

Emission Max.: 462.8 nm

Photoluminescence Efficiency (x,y): 0.002 cdm$^2$ μW$^{-1}$ (0.27, 0.36)

Reagents

Thorium(IV) chloride hydrate, 99.9%; Strem Chemicals; 09-3155

4-<sup>t</sup>Butylacetyl-3-methyl-1-phenyl-pyrazol-5-one; as prepared

Ethanol, denatured with 4.8% Methanol; Fluka; 02857

Example 6

Bis-(4-<sup>t</sup>Butylacetyl-3-methyl-1-phenyl-pyrazol-5-onato)Calcium (Ca($^t$BuPz)$_2$ (Ca($^t$BuPz)$_2$ was prepared by the method of Example using calcium chloride in place of the Terbium chloride.

Example 7

The (Tb($^t$BuPz)$_3$ of Example 4 was heated at reflux with diphenylphosphinic-azide in trimethyl pentane and the mixture heated to reflux until a clear solution was obtained (about 1 hour). The solution was allowed to clear yielding (Tb($^t$BuPz)$_3$)di phenylphosponimidetris-phenylphosphorane, (Tb($^t$BuPz)$_3$OPNP[Tb(pyr)$_3$OPNP] as a crystalline solid.

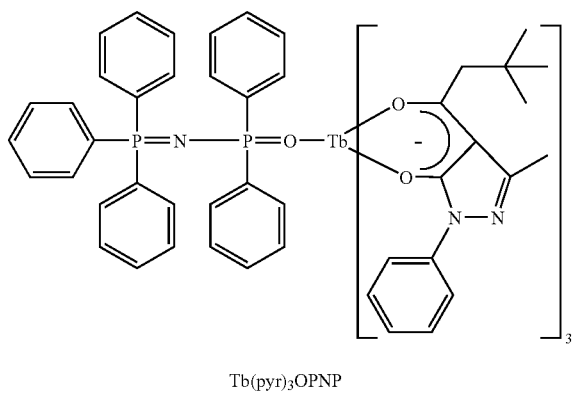

Tb(pyr)₃OPNP

Example 8

The Ca(ᵗBuPz)₂ of Example 6 was heated under reflux with 1,10-phenanthroline in chloroform overnight. The solvent was removed in vacuo to yield a solid which was Ca(ᵗBuPz)₂Phen₂[Ca(pyr)₂Phen₂].

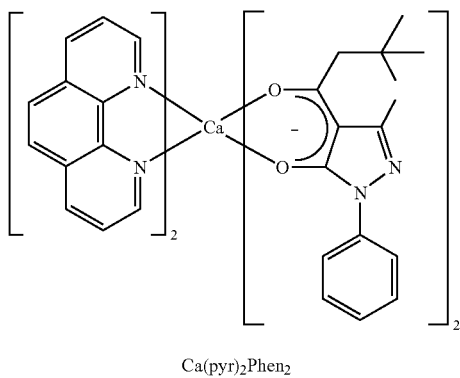

Ca(pyr)₂Phen₂

Device Fabrication

An indium tin oxide (ITO) coated glass piece (1×1 cm²) had a portion etched out with concentrated hydrochloric acid to remove the ITO and was cleaned and dried. Four devices were fabricated Device 1 was fabricated by sequentially forming on the ITO, layers comprising ITO/α-NPB(75 nm)/Tb(pyr)₃OPNP (50 nm)/BCP(20 nm)Alq₃(40 nm)LiF(0.5 nm/Al where α-NPB is in FIG. 1, BCP is bathocupron, LiF is lithium fluoride and Alq₃ is aluminium quinolate.

Device 2 was fabricated by sequentially forming on the ITO, layers comprising ITO/α-NPB(10 nm)/Tb(pyr)₃OPNP (50 nm)/BCP(20 nm)Alq₃(40 nm)LiF(0.7 nm/Al Device 3 was fabricated by sequentially forming on the ITO, layers comprising ITO(100 Ωsqr)/CuPc(8 nm)/α-NPB (60 nm)/Ca(pyr)₂Phen₂(50 nm)/Alq₃(10 nm)/LiF(0.7 nm)/Al where CuPc is copper phthalocyanine, Device 4 was fabricated by sequentially forming on the ITO, layers comprising ITO(100 Ωsqr)/CuPc(8 nm)α-NPB (60 nm)/Ca(pyr)₂Phen₂(10 nm)/Al The organic coating on the portion which had been etched with, the concentrated hydrochloric acid was wiped with a cotton bud. The coated electrodes were stored in a vacuum desiccator over a molecular sieve and phosphorous pentoxide until they were loaded into a vacuum coater (Edwards, $10^{-6}$ torr) and aluminium top contacts made. The active area of the LED's was 0.08 cm2 by 0.1 cm² the devices were then kept in a vacuum desiccator until the electroluminescence studies were performed.

The ITO electrode was always connected to the positive terminal. The current vs. voltage studies were carried out on a computer controlled Keithly 2400 source meter. Electroluminescence spectra were recorded by means of a computer controlled charge coupled device on PR650 system made by Photoresearch Inc.

The results are shown in FIGS. 16 to 23.

The invention claimed is:

1. An electroluminescent device comprising: (i) a first electrode; (ii) a second electrode; and, (iii) between said first and second electrodes, an electroluminescent layer comprising a compound selected from the group consisting of (Tb (ᵗBuPz)₃) diphenylphosphonimidetris-phenylphosphorane [Tb(pyr)₃OPNP] and bis(1,10-phenanthroline) calcium bis-(4-t-butylacetyl-3-methyl-1-phenyl-pyrazol-5onate) [Ca(pyr)₂Phen₂].

2. An electroluminescent device comprising: (i) a first electrode; (ii) a second electrode; and, (iii) between said first and second electrodes, an electroluminescent layer comprising (Tb(ᵗBuPz)₃) diphenylphosphonimidetris-phenylphosphorane [Tb(pyr)₃OPNP].

3. The device of claim 1, wherein the compound is bis(1,10-phenanthroline) calcium bis-(4-t-butylacetyl-3-methyl-1-phenyl-pyrazol-5onate) [Ca(pyr)₂Phen₂].

4. The device of claim 1, further comprising a hole transport layer of α-NPB between said first and second electrodes.

5. The device of claim 1, further comprising an electron transport layer of aluminum quinolate between said first and second electrodes.

6. An electroluminescent device comprising: (i) a first electrode; (ii) a second electrode; (iii) between said first and second electrodes, an electroluminescent layer comprising the compound bis(1,10-phenanthroline) calcium bis-(4-t-butylacetyl-3-methyl-1-phenyl-pyrazol-5onate) [Ca(pyr)₂Phen₂]; and, (iv) a hole transport layer of α-NPB between said first and second electrodes.

* * * * *